(12) United States Patent
Nilsson et al.

(10) Patent No.: US 7,718,379 B2
(45) Date of Patent: May 18, 2010

(54) IDENTIFYING HAEMATOPOIETIC STEM CELLS BASED ON CELL SURFACE MARKERS

(75) Inventors: Susan Kaye Nilsson, East Bentleigh (AU); Paul John Simmons, Kew (AU); David Norman Haylock, Melbourne (AU)

(73) Assignee: The Peter Maccallum Cancer Institute, East Melbourne (AU)

( * ) Notice: Subject to any disclaimer, the term of this patent is extended or adjusted under 35 U.S.C. 154(b) by 0 days.

(21) Appl. No.: 11/933,633

(22) Filed: Nov. 1, 2007

(65) Prior Publication Data

US 2008/0076148 A1    Mar. 27, 2008

Related U.S. Application Data

(63) Continuation of application No. 10/837,038, filed as application No. PCT/AU02/01443 on Oct. 24, 2002, now abandoned.

(30) Foreign Application Priority Data

Oct. 30, 2001  (AU) .................................... PR 8565

(51) Int. Cl.
  *G01N 33/53*  (2006.01)
  *C12N 5/08*  (2006.01)
(52) U.S. Cl. .................. 435/7.1; 435/372; 435/374
(58) Field of Classification Search .................. None
  See application file for complete search history.

(56) References Cited

U.S. PATENT DOCUMENTS

| | | | | |
|---|---|---|---|---|
| 6,875,753 B1 * | 4/2005 | Pilarski | ..................... | 514/54 |
| 2003/0032621 A1 | 2/2003 | Smadja-Joffe et al. | | |

FOREIGN PATENT DOCUMENTS

| | | | |
|---|---|---|---|
| WO | 9945942 | | 9/1999 |
| WO | WO 9945942 | * | 9/1999 |
| WO | 0017326 | | 3/2000 |
| WO | 0047163 | | 8/2000 |
| WO | 0244345 | | 6/2002 |

OTHER PUBLICATIONS

Campbell et al., Human Reproduction, 1995, v.10 pp. 425-430.*
Haegel et al., Develop.Immunol 1994, V.3 pp. 239-246.*
Furnus et al., Theriogenology, 2003, pp. 1633-1644.*
Aruffo et al., "CD44 Is the Principal Cell Surface Receptor for Hyaluronate" Cell, 61:1303-1313 (Jun. 29, 1990).
Prehm, "Identification and regulation of the eukaryotic hyaluronate synthase" The Biology of Hyaluronan, Wiley, Chichester (Ciba Foundation Symposium 143) pp. 21-40 (1989).
Toole et al., "Hyluronate and invasiveness of the rabbit V2 carcinoma" Proc. Natl. Acad. Sci. USA 76(12):6299-6303 (Dec. 1979).
Turley et al. "Ras-Transformed Cells Express Both CD44 and RHAMM Hyaluronan Receptors: Only RHAMM is Essential for Hyaluronan-Promoted Locomotion" Experimental Cell 207:277-292 (1993).
Nilsson et al., "Hyaluronan is synthesized by primitive hemopoietic cells, participates in their lodgment at the endosteum following transplantation, and is involved in the regulation of their proliferation and differentiation in vitro" Blood, 101(3):856-862 (Feb. 1, 2003).
Spangrude et al., "Long-Term Repopulation of Irradiated Mice With Limiting Numbers of Purified Hematopoetic Stem Cells: In Vivo Expansion of Stem Cell Phenotype But Not Function" Blood, 85(4):1006-1016 (Feb. 15, 1995).
Calabro et al., "Characterization of hyaluronan synthase expression and hyaluronan synthesis in bone marrow mesenchymal progenitor cells: predominant expression of HAS1 mRNA and up-regulated hyaluronan synthesis in bone marrow cells derived from multiple myeloma patients." Blood, 100:2578-2585 (2002).

* cited by examiner

*Primary Examiner*—Michail A Belyavskyi
(74) *Attorney, Agent, or Firm*—Karl Bozicevic; Bozicevic, Field & Francis LLP

(57) ABSTRACT

The present invention relates to a method of identifying a haematopoietic stem cell (HSC) or progeny thereof comprising the steps of: obtaining a cell sample including HSC or progeny thereof; detecting the presence of at least one carbohydrate sequence having a sequence of at least one disaccharide repeat of glucuronic acid and N-acetylglucosamine or an equivalent thereof; and identifying a HSC or progeny thereof having the sequence or equivalent thereof. The invention also relates to methods of enriching cell populations for HSC or progeny thereof, for isolating HSC or progeny thereof and cell preparations obtained using the methods of their invention and their uses.

5 Claims, 10 Drawing Sheets

EXPRESSION OF HA ON MURINE HSC
(lin-Sca+Kit+Cells)
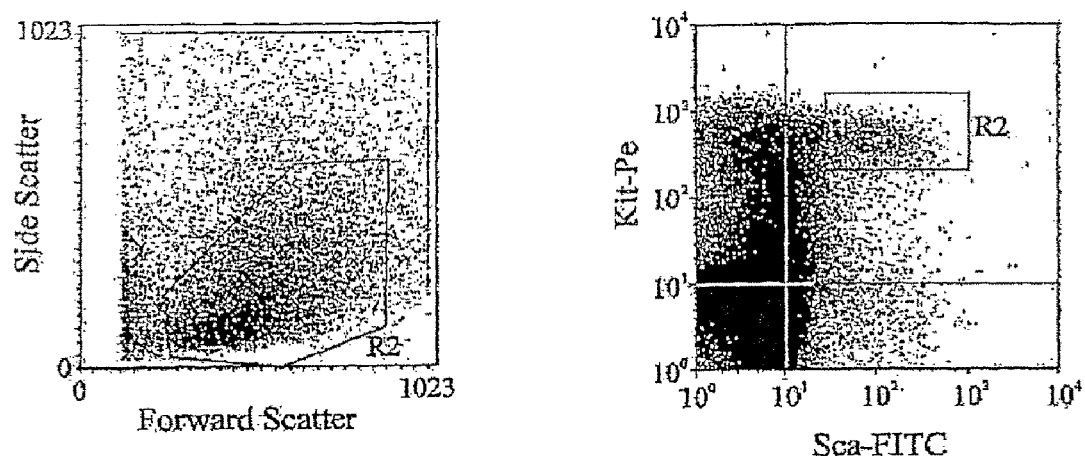
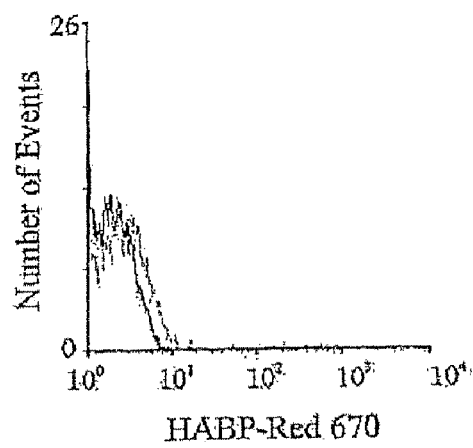
FIG 1A

HA EXPRESSION ON lin⁻ Rh$^{dull}$ HSC AND REMOVAL BY HY TREATMENT

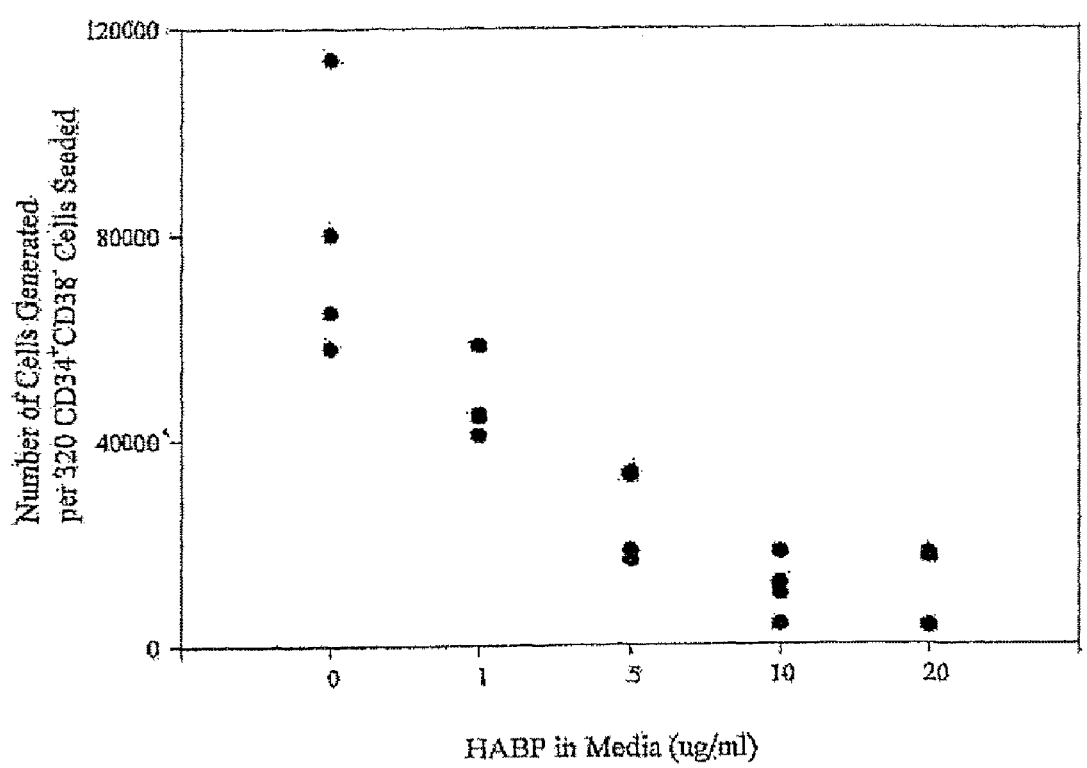
FIG 5A (ii)   HABP Growth Inhibition of $CD34^+CD38^-$ Cells

Differentiation of Cultured CD34+CD38- CB Cells
(1000 Cells Seeded per Well)

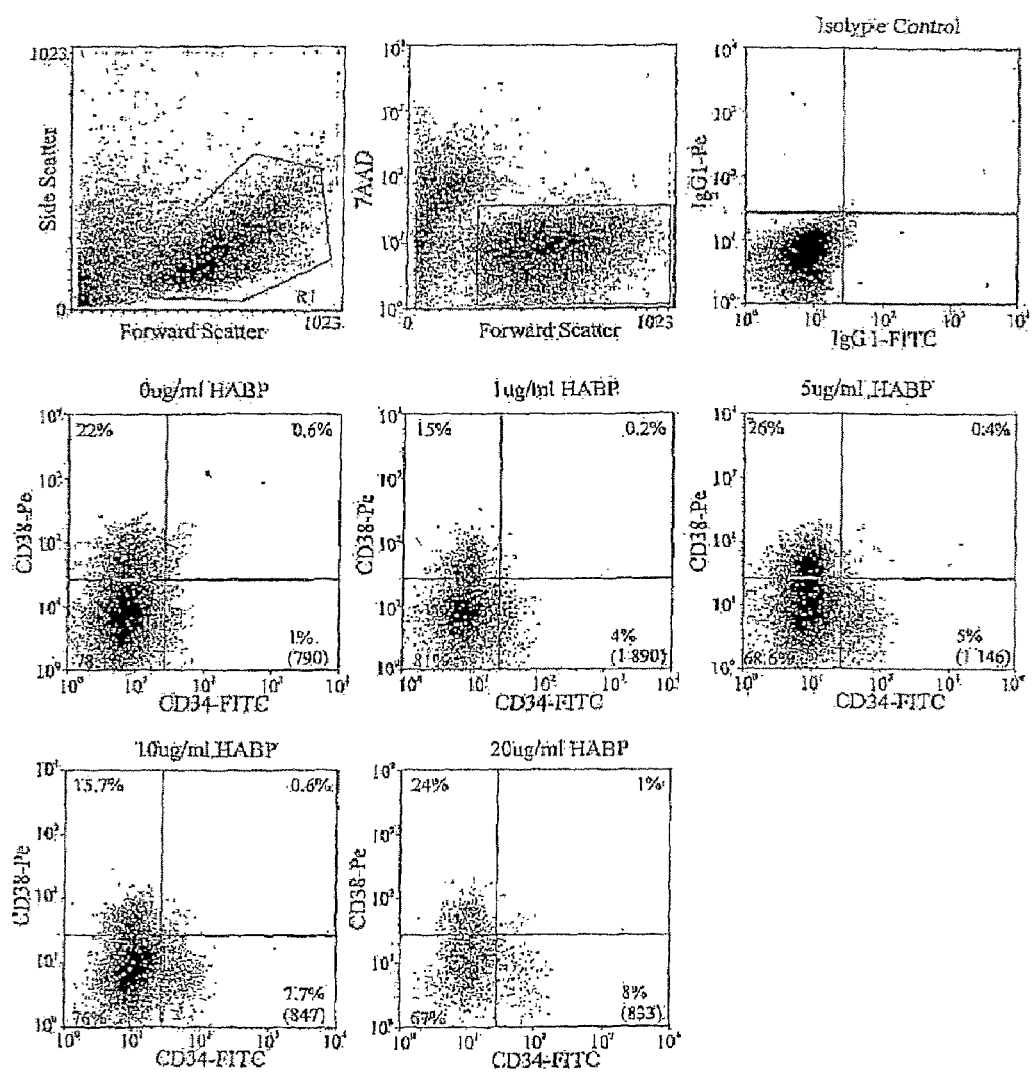

FLOW CYTOMETRY

IDENTIFYING HAEMATOPOIETIC STEM CELLS BASED ON CELL SURFACE MARKERS

This application is a continuation of U.S. patent application Ser. No. 10/837,038, filed Apr. 30, 2004 (now abandoned) which is a continuation-in-part of published PCT Application No. PCT/AU02/01443 filed Oct. 24, 2002 which claims priority to Australian Application No. PR 8565 filed Oct. 30, 2001 all of which applications are incorporated herein in their entirety and to which applications is claimed priority.

FIELD OF THE INVENTION

The present invention relates to the identification of a specific population of cell types, in particular, haematopoietic stem cells (HSC) and cells deriving from HSC. The invention also provides for methods of isolation and uses of the stem cells and their progeny derived from the methods. Methods of regulating development of the stem cells and their progeny are also provided.

BACKGROUND

There exist a strong interest in identifying specific cell types in an effort to gain enriched populations of the cells. Having possession of an enriched population may allow for a better understanding of the specific cell types or even provide uses in various situations including transplantation, gene therapy, treatment of disease including cancers such as leukaemias, neoplastic cancers including breast cancers, or repair of tissues and skin.

Stem cells give rise to cells, which ultimately contribute to various parts of the plant or animal. One type of stem cell is the haematopoietic stem cell.

Hematopoietic cells are responsible for an extraordinarily diverse range of activities. They are divided into several lineages, including lymphoid, myeloid and erythroid. The lymphoid lineage, comprising B cells and T cells, produces antibodies, regulates cellular immunity, and detects foreign agents such as disease-causing organisms in the blood. The myeloid lineage, which includes monocytes, granulocytes, and megakaryocytes, monitors the blood for foreign bodies, protects against neoplastic cells, scavenges foreign materials, and produces platelets. The erythroid lineage includes red blood cells, which carry oxygen.

Haematopoietic stem cells are capable of self-renewal, multilineage proliferation and differentiation, and long-term support of the haematopoietic and lymphoid systems. They form a subpopulation within the haematopoietic progenitor compartment (HPC), which mainly comprises cells of more limited potentiality. HPC cells are mainly located within the bone marrow stroma, where complex interaction with stromal cells, extracellular matrix components and cytokines, permits regulation of cell proliferation and differentiation. HPC cells are also present in the blood under a variety of physiological, pathological and iatrogenic circumstances. HPC can be harvested from bone marrow or peripheral blood, and will re-engraft the bone marrow following intravenous infusion in patients who have received ablative (i.e. destructive) doses of chemotherapy and/or radiotherapy, leading to regeneration of haematopoiesis and immunity. Thus, HPC cell transplantation is of considerable clinical utility in the management of patients with haematological and solid malignancies, bone marrow failure, and inborn errors of haematopoiesis, immunity or metabolism.

There is thus a need for supplies of autologous HPC cells which may be cultured in vitro prior to reintroduction into a patient whose HPC cell population has been depleted due to chemotherapy and/or radiotherapy. The populations of such HPC cells may take many weeks or months to recover naturally to their normal levels. The use of autologous cells from the patient themselves avoids rejection of the transplanted cells.

In vivo, HPC cells are generally located within the bone marrow stroma. In vitro, HPC cells are able to adhere to bone marrow stromal layers before proliferating and releasing more committed progenitors. Stem cells undergo marked proliferation and differentiation into multiple lineages, ultimately giving rise to fully differentiated cells or progeny, such as red blood cells, platelets, a variety of white blood cells, and also immune cells such as T lymphocytes and B lymphocytes. Thus, the reintroduction of HPC cells or stem cells into the patient who is depleted therein, allows efficient repopulation of these haematopoietic cell types.

The relative paucity of hematopoietic stem cells has prevented extensive research on stem cells and hematopoietic differentiation in general. The ready availability of a cell population enriched in hematopoietic stem cells would make possible the identification of biological modifiers affecting stem cell behavior. For example, there may be as yet undiscovered growth factors associated with (1) early steps of dedication of the stem cell to a particular lineage; (2) the prevention of such dedication; and (3) the ability to control stem cell proliferation.

The availability of sufficient numbers of stem cells in an enriched population would also be extremely useful, for example, in reconstituting hematopoiesis in patients undergoing treatments which destroy stem cells, such as cancer chemotherapy.

Considerable evidence supports the proposal that the localization of hemopoiesis to the bone marrow (BM) in adult mammals involves developmentally regulated interactions between primitive hematopoietic stem cells (HSC) and the stromal cell mediated hemopoietic microenvironment (HM) of the marrow.

Anatomical location of maturing hemopoietic cells within the BM is better understood than the spatial distribution of more primitive cells. Previous studies in the mouse have established that lineage restricted clonogenic hemopoietic progenitor cells (HPC) also conform to a well-defined spatial distribution across the axis of the femur with greatest numbers near the central longitudinal vein. In contrast, hierarchically more primitive progenitors, colony-forming unit spleen (CFU-S), exhibit the converse distribution with low numbers in the central region of the marrow and greatest enrichment in a region adjacent to bone the endosteum.

The reestablishment of hemopoiesis by intravenously infused cells requires several coordinated events including homing, migration and lodgement of HPC within the BM HM. The initial event, homing, is the specific recruitment of circulating HSC to the BM and involves the selective recognition of HSC by the microvascular endothelium of the marrow and trans-endothelial cell migration into the extravascular hemopoietic space. In contrast, lodgement encompasses events following extravasation and is defined as the selective migration of cells to suitable HM niches in the extravascular compartment. Current data suggests that homing involves a similar cascade of cell adhesion molecules (CAMs) to those participating in the extravasation of mature leukocytes into tissues. Primitive hemopoietic cells exhibit a broad repertoire of CAMs including various members of the integrin, sialomucin, Ig super family and CD44 families. Current data suggest key roles for the sialomucin receptor for P-selectin, PSGL-1, the $\beta_1$ integrin VLA-4 and the receptor for SDF-1, CXCR4 in HSC homing to the BM. In contrast, very little is known about the molecules that influence the site of HSC lodgement following homing to the BM.

However, identification of these specific cell types by cell surface markers has generally proven to be the best means of identification. The identification of additional cell surface antigens would clearly be of major value in the identification, isolation and further characterization of hematopoietic stem cells.

Until recently, it has not been possible to define the spatial distribution of hemopoietic stem cells (HSC) within the BM. This is due to the rarity of HSC and the lack of a single, unique antigenic marker allowing their unambiguous identification in situ.

Accordingly, it is an object of the present invention to overcome or at least alleviate some of the problems of the prior art.

SUMMARY OF THE INVENTION

Applicants have found that hyaluronic acid (HA) and hyaluronic acid synthase (HAS) is expressed in hematopoietic stem cells (HSC). HA is a high molecular weight linear carbohydrate generally found in the extracellular matrix of many cells.

In an aspect of the present invention there is provided a method of identifying a HSC or progeny thereof comprising the steps of:
 obtaining a cell sample including HSCs or progeny thereof;
 detecting the presence of HA or HAS or a fragment thereof on a cell; and
 identifying the HSCs or progeny thereof having HA or HAS or a fragment thereof on the cell.

Any means of identifying the HA or HAS or equivalent or fragment thereof may be used. However, in a preferred aspect of the present invention there is provided a method of identifying a HSC or progeny thereof comprising the steps of:
 obtaining a cell sample including HSCs or progeny;
 combining the sample with an antibody for HA or HAS or fragment thereof;
 detecting the presence of HA or HAS or a fragment thereof; and
 identifying the HSCs or progeny thereof having HA or HAS or fragment thereof by detecting the presence of the antibody on the HSCs or progeny thereof.

Preferably, the antibody is any antibody specific for HA or HAS or fragment thereof. The antibody used in the present invention encompasses any antibody or fragment thereof, either native or recombinant, synthetic or naturally-derived, monoclonal or polyclonal which retains sufficient specificity to bind specifically to the HA or HAS or a fragment thereof which is indicative of HA.

In yet another preferred aspect of the present invention there is provided a method of identifying a HSC or progeny thereof comprising the steps of:
 obtaining a cell sample including HSC or progeny thereof;
 combining the sample with a binding protein for HA or HAS or a fragment thereof;
 detecting the presence of the binding protein; and
 identifying the HSC or progeny thereof having HA or HAS or a fragment thereof by detecting the presence of the binding protein on the HSC or progeny thereof.

Binding protein, especially HA binding protein (HABP) is useful for detecting HA. HABP may be obtained from Seikagaku Corporation. However, any equivalent based on the binding protein properties may be used to identify the HA. It is conceivable that the binding portions of the binding protein are identified and synthetically prepared as an indicator or HA. Accordingly, synthetic indicators based on the HABP are within the scope of the present invention.

The present invention also encompasses a method for obtaining a cell population enriched in HSCs or progeny thereof comprising the steps of
 obtaining a cell population comprising HSCs or progeny thereof;
 detecting the presence of HA or HAS or a fragment thereof on a cell; and
 selecting for cells which are identified by the presence of HA or HAS or a fragment thereof on the cell.

Preferably the method of detection involves the use of an antibody to HA or HAS; or a binding protein (HABP) to HA can also be used to detect HA or equivalents thereof.

Similarly, in another preferred embodiment, there is provided a method of removing HSCs or progeny thereof from a population comprising the steps of
 obtaining a cell population comprising HSCs or progeny thereof;
 detecting the presence of HA or HAS or a fragment thereof on a cell; and
 selecting out those cells which are identified by the presence of HA or HAS or a fragment thereof on the cell.

Again, the use of antibodies or HABP to detect HA or HAS prior to selection may also be employed.

The methods described herein may also be used to isolate HSCs or progeny thereof from cell populations or measure HSC content in such populations. Once a HSC is isolated or identified, they may be used in methods of treating or diagnosing HSC related or associated conditions or further isolation techniques may be employed to isolate subpopulations within the HSC populations. Specific markers for specific cell lineages such as lymphoid, myeloid or erythroid cells may be used to identify and isolate the various cell lineages.

FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1a shows expression of HA on murine HSC (Lin$^-$Sca$^+$Kit$^+$ cells).

FIG. 5a(ii) shows growth inhibition in human HSC.

FIG. 5b(ii) shows phenotypic analysis of cultured CD34$^+$ CD38$^-$ CB cell.

DETAILED DESCRIPTION OF PREFERRED EMBODIMENTS

Figure 1B:
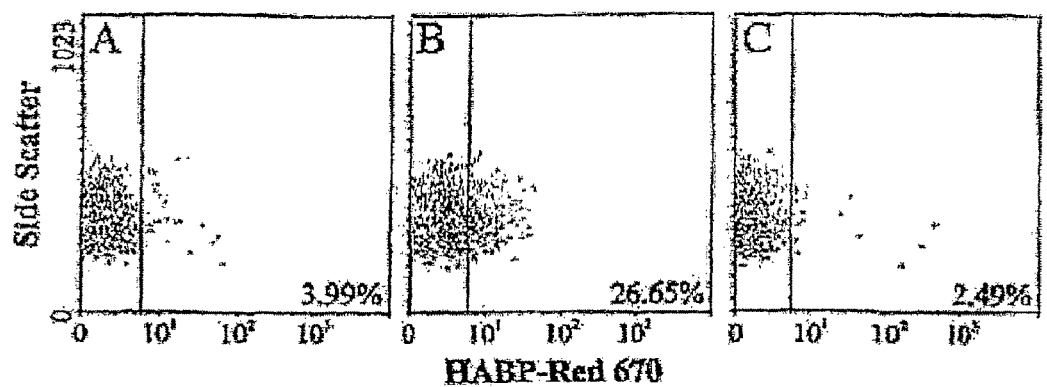
FIG. 1b shows HA expression on Lin$^-$Rh$^{dull}$HSC and removal by HY treatment.

Before the present detection system and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a cell" includes a plurality of such cells and reference to "the sequence" includes reference to one or more sequences and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

INVENTION IN GENERAL

In one aspect of the present invention there is provided a method of identifying a HSC or progeny thereof comprising the steps of
obtaining a cell sample including HSC or progeny thereof;
detecting the presence of at least one carbohydrate sequence having a sequence of at least one disaccharide repeat of glucuronic acid and N-acetylglucosamine or an equivalent thereof, and
identifying a HSC or progeny thereof having the sequence or equivalent thereof.

The carbohydrate sequences described herein have been found to be expressed specifically on HSC or progeny thereof. The sequence includes at least one repeat unit of disaccharide wherein the unit includes glucuronic acid and N-acetylglucosamine or an equivalent thereof. Several repeat disaccharide units may be joined as a continuous molecule of disaccharide repeats to provide a linear molecule or the carbohydrate repeats may be interspersed with molecules which are not disaccharides of glucuronic acid and N-acetylglucosamine or an equivalent thereof. However, the HSC or progeny thereof can be identified by at least one repeat disaccharide providing at least 2 disaccharide units are at least 4 saccharides comprising, in order, glucuronic acid and N-acetylglucosamine or an equivalent thereof, then glucuronic acid and N-acetylglucosamine or an equivalent thereof.

The term "equivalent" thereof as used herein means a sequence or molecule which functions in a similar way but may have deletions, additions or substitutions that do not substantially change the activity or function of the sequence or molecule.

In another aspect of the present invention there is provided a method of identifying a HSC or progeny thereof comprising the steps of:
obtaining a cell sample including HSC or progeny thereof;
detecting the presence of HA or HAS or a fragment thereof on a cell; and
identifying the HSC having HA or HAS or a fragment thereof on the cell.

Applicants have shown that HSC and progeny thereof synthesize and express HA. HA synthesis and expression was found in multiple mammalian systems, and may be expressed mainly into primitive hematopoietic cells. HA was found to be critical in the lodgment of transplanted HSC within the bone marrow, with its specific removal using hyaluronidase significantly altering their spatial distribution. In addition, the binding of HA on the surface of HSC to a surrogate ligand in vitro results in a profound suppression of HSC proliferation and differentiation.

The molecule or molecules associated with its production have not previously been connected to HSC nor for their identification. In particular, the molecule has not been associated with expression from a HSC or progeny thereof.

HA is single-chain high molecular-mass polysaccharide of repeating disaccharide units (glucuronic acid and N-acetylglucosamine) which is synthesised by one of 3 hyaluronic acid synthases (HAS), encoded by one of 3 HAS genes (Has 1, Has 2, Has 3). The latter are integral membrane glycosyltransferases, located at the plasma membrane and translocate HA as a free linear polymer to the pericellular space, not covalently linked to proteins on the cell surface. Accordingly, HA is present in many different organs and is a component of the ECM within the BM microenvironment. Cell surface HA significantly affects the adhesion, motility and growth of a wide variety of cell types, both normal and neoplastic. Due to its multivalency (which allows cross bridging of multiple receptors on adjacent cells), the interaction of endogenous cell surface HA with its primary receptor, CD44, mediates aggregation of several cell types. Increased cell movement or invasion may follow either the exposure of cells to HA, or the ectopic expression of HA or HAS. Moreover, inhibition of cell movement also occurs as a consequence of either HA degradation or the blocking of HA receptors. HA also influences cell proliferation, differentiation and tissue repair and HA may be implicated in the pathogenesis and dissemination of tumours.

HA or HAS or a fragment of HAS may be detected on the HSC. Preferably the HA or HAS molecule is detected. However, fragments of the HAS molecule may also be indicative of HA. Such fragments may include peptide sequences corresponding to portions of the HAS molecule or an equivalent thereof.

Throughout the description and claims of this specification, the word "comprise" and variations of the word, such as "comprising" and "comprises", is not intended to exclude other additives, components, integers or steps.

The sample of HSC or progeny thereof may originate from any source including an embryonic or adult source. Preferably, the HSC source is from the bone marrow including iliac crests, tibiae, femors, spine, periosteum, endosteum or other bone cavities. The HSC may also be derived from blood, embryonic yolk sac, fetal liver, spleen, peripheral, blood, skin, dermis, or may be derived from ES cells or ES cell cultures.

The sample may be a tissue sample or a cell suspension or cells derived from either source grown in vitro which allows for interaction of a marker for HA or HAS or fragment thereof to identify the HSC or progeny thereof. The sample may also be enriched for CD34+ cells prior to detection of HA or HAS or fragment thereof.

For isolation of bone narrow, an appropriate solution can be used to flush the bone, including, but not limited to, salt solution, conveniently supplemented with fetal calf serum (FCS) or other naturally occurring factors, in conjunction with an acceptable buffer at low concentration, generally from about 5-25 mM. Convenient buffers include, but are not limited to, HEPES, phosphate buffers and lactate buffers. Otherwise bone marrow can be aspirated from the bone in accordance with conventional techniques.

The term "progeny" as used herein includes all cells deriving from HSC and includes primitive cells which have not differentiated or specialized to any particular cell type. Various methods and products for manipulating haematopoietic stem cells and descriptions of such cells are described and disclosed in a number of publications including WO 02/44345 A1 published Jun. 6, 2002. Further, see descriptions for various means for regulating haematopoietic differentiation within published PCT application WO 00/47163 published Aug. 17, 2000. Still further, see a description of various non-haematopoietic cells including cardiomyocytes, skeletal muscle cells, derived from human haematopoietic cells and methods of making and using them as described within published PCT WO 00/17326 published Mar. 30, 2000 all of which PCT published applications are incorporated herein by reference in their entirety as are the various patents and other publications cited within them in order to describe and disclose haematopoietic cells and their progeny and related technologies.

The method of detecting HA or HAS or fragment thereof will be dependent upon the type of sample including the HSC or progeny thereof. Generally the sample is exposed or combined with a marker for HA or HAS or fragment thereof in a manner which facilitates the marker interaction with the cells. For example, where the sample is a cell suspension as in a blood sample, the marker may simply be added to the cell suspension. This is applicable where the marker is intended to physically identify HA or HAS or fragment thereof.

The marker for HA or HAS or fragments thereof may include any means which identifies HA or HAS or fragments thereof, preferably it is a marker which identifies HA or HAS or fragments thereof on a cell surface which includes but is not limited to antibodies to HA or HAS or fragments thereof, agonists and antagonists against HA or HAS or fragments thereof, binding proteins to HA such as hyaluronic binding protein (HABP) or HAS or fragments thereof, nucleic acid detection systems which can detect expression of HA or HAS either by the presence of DNA, RNA, mRNA or HA or HAS protein, and enzymatic, fluorescence or colourimetric assays for HA or HAS or fragments thereof. Binding protein or ligands which bind to HA or HAS or fragments thereof and which may be immobilised may serve as a means for isolation and identification of HA positive cells. Techniques such as panning may utilize these approaches to isolation and identification of HA positive cells. The method of detection will be apparent to the skilled addressee for the type of marker selected.

The marker may include the addition of labels to enhance the identification of the marker. For instance, fluorescence, radioactivity or enzymatic markers familiar to the skilled addressee may be linked to the marker to enhance detection.

The term "fragment thereof" as it applies to HAS includes portions of HAS which can still identify HAS but is not the full HAS molecule. Examples of this includes epitopes of HAS or active portions of HAS which provide identity to HAS.

In a preferred aspect of the present invention there is provided a method of identifying a HSC or progeny thereof comprising the steps of:
obtaining a cell sample including HSC or progeny thereof;
combining the sample with a binding protein for HA or HAS or a fragment thereof;
detecting the presence of the binding protein; and
identifying the HSC or progeny thereof having HA or HAS or a fragment thereof by detecting the presence of the binding protein on the HSC or progeny thereof.

Binding protein, especially HA binding protein (HABP) is useful for detecting HA. HABP may be obtained from Seikagaku Corporation. However, any equivalent based on the binding protein properties may be used to identify the HA. It is conceivable that the binding portions of the binding protein are identified and synthetically prepared as an indicator or HA. Accordingly, synthetic indicators based on the HABP are within the scope of the present invention.

Use of HABP may be in accordance with the directions given by the manufacturer. However, the binding protein may be further labelled to facilitate the identification of the bound HABP to HSC or their progeny.

In another preferred aspect of the present invention there is provided a method of identifying a HSC or progeny thereof comprising the steps of:
obtaining a cell sample including HSC or progeny thereof;
combining the sample with an antibody for HA or HAS or a fragment thereof,
detecting the presence of the antibody; and
identifying the HSC or progeny thereof having HA or HAS or a fragment thereof by detecting the presence of the antibody on the HSC or progeny thereof.

Preferably, the antibody is any antibody specific for HA or HAS or a fragment thereof. The antibody used in the present invention encompasses any antibody or fragment thereof, either native or recombinant, synthetic or naturally-derived, monoclonal or polyclonal which retains sufficient specificity to bind specifically to the HA or HAS or a fragment thereof which is indicative of HA or HAS. As used herein, the terms "antibody" or "antibodies" include the entire antibody and antibody fragments containing functional portions thereof. The term "antibody" includes any monospecific or bispecific compound comprised of a sufficient portion of the light chain variable region and/or the heavy chain variable region to effect binding to the epitope to which the whole antibody has binding specificity. The fragments can include the variable region of at least one heavy or light chain immunoglobulin polypeptide, and include, but are not limited to, Fab fragments, F(ab')$_2$ fragments, and Fv fragments.

The recombinant antibody can be produced by any recombinant means known in the art. Such recombinant antibodies include, but are not limited to, fragments produced in bacteria and non-human antibodies in which the majority of the constant regions have been replaced by human antibody constant regions. In addition, such "humanized" antibodies can be obtained by host vertebrates genetically engineered to express the recombinant antibody.

In addition, the monospecific domains can be attached by any method known in the art to another suitable molecule compound. The attachment can be, for instance, chemical or by genetic engineering.

The antibodies can be conjugated to other suitable molecules and compounds including, but not limited to, enzymes, magnetic beads, colloidal magnetic beads, haptens, fluorochromes, metal compounds, radioactive compounds, chromatography resins, solid supports or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P. Molecular Probes: Handbook of Fluorescent Probes and Research Chemicals (1992-1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include but are not limited to technetium 99m, $^{125}$I and amino acids comprising any radionuclides, including, but not limited to $^{14}$C, $^{3}$H and $^{35}$S.

The antibodies to HA or HAS or fragments thereof may be obtained by methods known in the art for production of antibodies or functional portions thereof. Such methods include, but are not limited to, separating B cells with cell-surface antibodies of the desired specificity, cloning the DNA expressing the variable regions of the light and heavy chains and expressing the recombinant genes in a suitable host cell. Standard monoclonal antibody generation techniques can be used wherein the antibodies are obtained from immortalized antibody-producing hybridoma cells. These hybridomas can be produced by immunizing animals with HSCs or progeny thereof, and fusing B lymphocytes from the immunized animals, preferably isolated from the immunized host spleen, with compatible immortalized cells, preferably a B cell myeloma.

Antibodies to HA or HAS or fragments thereof may be obtained from any source. They may be commercially available. Effectively, any means which detects the presence of HA or HAS or fragments of HA or HAS on the cells is with the scope of the present invention. An example of such an antibody is a pan-species αHA polyclonal sheep antibody from Biogenesis.

The methods outlined herein are particularly useful for identifying HSCs or progeny thereof from a population of cells. However, additional markers may be used to further distinguish subpopulations within the general HSC population. Preferably, a pre-enrichment step for CD34$^+$ cells is made by methods used in the art. Following this step, HA or HAS determination may be made.

The step of using additional markers may be applied separately or in combination with a marker for HA or HAS or a fragment thereof.

The various sub-populations may be distinguished by levels of expression of HA or HAS. This may manifest as expressed HA on the cell surface which may be detected by the methods outlined herein. However, the present invention may be used to distinguish between various phenotypes of the HSC population including, but not limited to, the CD34$^+$, CD38$^-$, CD90$^+$ (thy 1) and Lin$^-$ cells. Preferably the cells identified are selected from the group including, but not limited to, CD34$^+$, CD38$^-$, CD90+ (thy 1), or Lin$^-$.

In another aspect of the present invention, there is provided a method for obtaining a cell population enriched in HSC or progeny thereof comprising the steps of obtaining a cell population comprising HSC or progeny thereof;

detecting the presence of HA or HAS or a fragment thereof on a cell; and selecting for cells which are identified by the presence of HA or HAS or a fragment thereof on the cell.

The present invention thus encompasses methods of enriching a population for HSCs or progeny thereof. The methods involve combining a mixture of HSCs or progeny thereof with an antibody or marker or binding protein that recognizes and binds to HA or HAS or fragments thereof under conditions which allow the antibody or marker to bind to HA or HAS or a fragment thereof and separating the cells recognized by the antibody or marker to obtain a population substantially enriched in HSCs or progeny thereof. The methods can be used as a diagnostic assay for the number of HSCs or progeny thereof in a sample. The cells and antibody or marker are combined under conditions sufficient to allow specific binding of the antibody or marker to HA or HAS and the HSCs or progeny thereof which are then quantitated. The HSCs or progeny thereof can be isolated or further purified.

Preferably, the marker is a HA binding protein (HABP) which binds to HA. A suitable source of HABP is Seigaku Corporation.

As discussed above the cell population may be obtained from any source of HSCs or progeny thereof including those samples discussed above.

The detection for the presence of HA or HAS or a fragment thereof may be conducted in any way to identify HA or HAS on the cells. Preferably the detection is by use of a marker or binding protein for HA or HAS. The marker for HA or HAS may be any of the markers discussed above. However, antibodies or binding proteins to HA or HAS are particularly useful as a marker for HA or HAS.

As discussed above, HA or HAS or a fragment of HA or HAS may be detected. Preferably the whole molecule of HA or HAS will be detected. However, it is conceivable that portions of the molecule which distinguish the molecule will be equally as effective.

Various techniques can be employed to separate or enrich the cells by initially removing cells of dedicated lineage. Monoclonal antibodies and binding proteins are particularly useful for identifying cell lineages and/or stages of differentiation. The antibodies can be attached to a solid support to allow for crude separation. The separation techniques employed should maximize the retention of viability of the fraction to be collected. Various techniques of different efficacy can be employed to obtain "relatively crude" separations. The particular technique employed will depend upon efficiency of separation, associated cytotoxicity, ease and speed of performance, and necessity for sophisticated equipment and/or technical skill.

Procedures for separation or enrichment can include, but are not limited to, magnetic separation, using antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique.

The use of separation or enrichment techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye, Hoescht 33342).

Techniques providing accurate separation include, but are not limited to, FACS, which can have varying degrees of sophistication, e.g., a plurality of color channels, low angle and obtuse light scattering detecting channels, impedence channels, etc. Any method which can isolate and distinguish these cells according to levels of expression of HA may be used.

In a first separation, typically starting with about $1 \times 10^{10}$, preferably at about $5 \times 10^{8-9}$ cells, antibodies or binding proteins to HA or HAS or fragments thereof can be labeled with at least one fluorochrome, while the antibodies or binding proteins for the various dedicated lineages, can be conjugated to at least one different fluorochrome. While each of the lineages can be separated in a separate step, desirably the lineages are separated at the same time as one is positively selecting for HA or HAS and/or other HSC markers. The cells can be selected against dead cells, by employing dyes associated with dead cells (including but not limited to, propidium iodide (PI)).

While it is believed that the particular order of separation is not critical to this invention, the order indicated is preferred. Preferably, cells are initially separated by a coarse separation, followed by a fine separation, with positive selection with antibodies to HA or HAS or fragments thereof. It is preferred that a pre-enrichment step is applied which enriches CD34+ cells prior to identification of HA or HAS.

In a preferred aspect of the present invention there is provided a method of obtaining a cell population enriched in HSCs or progeny thereof comprising the steps of:

obtaining cell populations comprising HSCs or progeny thereof;

combining the cell population with a binding protein for HA or HAS or a fragment thereof; and selecting for cells which are identified by the presence of the binding protein which is indicative of HA or HAS or a fragment thereof on the cell.

The binding protein is as described above.

In a preferred aspect of the present invention there is provided a method of obtaining a cell population enriched in HSCs or progeny thereof comprising the steps of:

obtaining cell populations comprising HSCs or progeny thereof;

combining the cell population with an antibody for HA or HAS or a fragment thereof; and selecting for cells which are identified by the presence of the antibody which is indicative of HA or HAS or a fragment thereof on the cell.

Any separation methods employing antibodies to isolate cells may be utilised and are familiar to the skilled addressee. The description above for identification of HSCs or progeny thereof is applicable here.

To further enrich for any cell population, specific markers for those cell populations may be used. For instance, specific markers for specific cell lineages such as lymphoid, myeloid or erythroid lineages may be used to enrich for or against these cells. These markers may be used to enrich for HSCs or progeny thereof by removing or selecting out mesenchymal or keratinocyte stem cells.

The methods described above can include further enrichment steps for cells by positive selection for other stem cell specific markers. Suitable positive stem cell markers include, but are not limited to, $CD34^+$, $Thy-1^+$, and $c-kit^+$. By appropriate selection with particular factors and the development of bioassays which allow for self-regeneration of HSCs or progeny thereof and screening of the HSCs or progeny thereof as to their markers, a composition enriched for viable HSCs or progeny thereof can be produced for a variety of purposes.

In yet another aspect of the present invention, there is provided an enriched population of HSCs or progeny thereof prepared by the methods described herein.

Similarly, in another preferred embodiment, there is provided a method of removing HSC or progeny thereof from a population comprising the steps of obtaining a cell population comprising HSC or progeny thereof;

detecting the presence of HA or HAS or a fragment thereof on a cell; and selecting out those cells which are identified by the presence of HA or HAS or a fragment thereof on the cell.

In the same manner as the enrichment, the use of HA or HAS may be reversed to provide a population substantially devoid of HSCs or progeny thereof. The method used above to select for those cells expressing HA or HAS can be used to select out the same cells leaving a population stripped of the HSCs or progeny thereof.

Preferably, HA or HAS is detected by using an antibody or binding protein to HA or HAS or a fragment thereof. More preferably, the HA is detected by the binding protein HABP. Once the marker, binding protein or antibody is attached to the HSC or progeny thereof, any method described above for isolation may be used to distinguish and select out for HSC or progeny thereof.

In yet another aspect of the present invention, there is provided a cell population having a decreased HSC population relative to a control cell population which has not undergone negative selection for HSC or progeny thereof.

In yet another aspect of the present invention, there is provided a method of isolating a HSC or progeny thereof comprising obtaining a cell population comprising HSC or progeny thereof;

detecting the presence of HA or HAS or a fragment thereof on a cell;

selecting for those cells which are identified by the presence of HA or HAS or a fragment thereof on the cell; and isolating those cells identified by the presence of HA or HAS or a fragment thereof.

The HSCs or progeny thereof may be isolated by any of the methods used for enrichment as described above with the added step of isolating the HSC. Useful techniques include magnetic separation, using antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique. Persons skilled in the art would be familiar with these techniques and can employ any known techniques providing HA or HAS is selected for.

In another preferred aspect there is provided a method of isolating a HSC or progeny thereof comprising obtaining a cell population comprising HSC or progeny thereof;

combining the cell population with a binding protein for HA or HAS or fragment thereof;

selecting for those cells which are identified by the binding protein for HA or HAS or fragment thereof; and isolating those cells identified by the antibody.

The binding protein is as described above.

In another preferred aspect there is provided a method of isolating a HSC or progeny thereof comprising obtaining a cell population comprising HSC or progeny thereof;

combining the cell population with an antibody for HA or HAS or fragment thereof;

selecting for those cells which are identified by the antibody for HA or HAS or fragment thereof; and isolating those cells identified by the antibody.

Any antibody presently available which is specific for HA or HAS may be used. A suitable antibody is a pan-species αHA polyclonal sheep antibody from Biogenesis.

Once the HSC or progeny thereof population is isolated, further isolation techniques may be employed to isolate subpopulations within the HSCs or progeny thereof. Specific markers including cell selection systems such as FACS for cell lineages may be used to identify and isolate the various cell lineages.

In another aspect there is provided a HSC or progeny thereof isolated by the methods described herein. Preferably the cell is $CD34^+$, $HA^+$. More preferably, the cell is $CD34^+$, thy1, $HA^+$. Most preferably, the cell is $CD34^+$, $CD38^-$, $thy1^+$, $HA^+$.

The present invention also provides in another aspect, a composition of enriched HSC and progeny thereof comprising an enriched population of cells including $CD34^+$, $CD38^-$, $thy1^+$, and $HA^+$ cells.

Where the compositions are enriched for HSC or progeny thereof, these may be used in autologous engraftment. Further, the use of autologous HSCs or progeny thereof will avoid graft-versus-host disease. In addition, the cells can be modified by appropriate gene transfer, to correct genetic defects or provide genetic capabilities naturally lacking in the HSCs or progeny thereof or their progeny, either as to the individual or as to the HSC generally. In addition, the HSC composition can be used to isolate and define factors associated with their regeneration and differentiation.

In yet another aspect of the present invention there is provided a method of measuring the content of HSC or their progeny said method comprising obtaining a cell population comprising HSC or progeny thereof;

combining the cell population with a binding protein for HA or HAS or fragment thereof;

selecting for those cells which are identified by the binding protein for HA or HAS or fragment thereof; and quantifying the amount of selected cells relative to the quantity of cells in the cell population prior to selection with the binding protein.

The binding protein is as described above.

In yet another aspect of the present invention there is provided a method of measuring the content of HSC or progeny thereof said method comprising obtaining a cell population comprising HSC or progeny thereof; combining the cell population with an antibody for HA or HAS or fragment thereof;

selecting for those cells which are identified by the antibody for HA or HAS or fragment thereof; and quantifying the amount of selected cells relative to the quantity of cells in the cell population prior to selection with HA or HAS antibody.

Quantifying the amount of selected HSCs or progeny thereof provides for a means of diagnosis of a HSC associated condition such as, but not limited to normal and malignant conditions or more specifically, leukaemia, carcinomas, or sarcomas or general infections which can cause an increase in the activity of HSC or their progeny, particularly in the haematopoietic stem cell populations, more specifically in the lymphoid lineages of those populations. In particular, the quantitation may provide an indication of the B and T cells which may differentiate from the lymphoid lineages to provide for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers.

The method may be performed by comparing the antibody treated sample having the HSC or their progeny identified from the cell population with a non-treated sample to identify that component which comprises the HSC. The whole cell numbers can be counted in the control. For diagnostic purposes it is considered that multiple samples may be measured and the fluctuations of cell numbers compared to monitor increasing or decreasing levels of HSC or their progeny.

In yet another aspect of the present invention there is provided a composition for detecting HSC or progeny thereof in a population, said composition comprising an indicator of HA or HAS or a fragment thereof and a carrier.

The indicator of HA or HAS or fragment thereof may include any detection means which can identify HA or HAS or a fragment thereof on a HSC or progeny thereof. Preferably the indicator is an antibody or binding protein to HA or HAS or a fragment thereof. The binding protein may be HABP.

The antibody may detect the full molecule of HA or HAS or detect specific peptide sequences contained within HAS which are indicative of HAS.

The composition may also comprise additional markers to distinguish specific cell lineages.

The invention also provides for methods of diagnosing conditions associated with HSCs or progeny thereof by identifying the presence of HSC or progeny thereof in a cell population. For instance, increased or decreased levels of haematopoietic stem cells may indicate abnormalities in the blood. This may be important in diseases such as leukaemia, similarly, increases may translate to increase in HSCs or progeny thereof differentiating to lymphoid lineages including T and B cells indicating infection. Other methods may measure HA or HAS expression on leukemia or other malignancies.

In yet another aspect of the present invention there is provided a method of controlling proliferation and/or differentiation in a HSC or progeny thereof, said method comprising modulating expression and/or activity of HA or HAS or a fragment thereof in a HSC or progeny thereof.

Applicants have found that HA or HAS is expressed in the HSC or progeny thereof. Prior to proliferation, levels of expression of HA or HAS change consistent with subsequent proliferation or differentiation of the cell. By modulating the expression and/or activity of HA or HAS in the cell, proliferation or differentiation of the cell may be controlled.

By the term "modulating expression and/or activity of hyaluronic acid" as used herein means modifying or altering the expression and/or activity of HA or HAS compared to unmodified levels.

The phrase "controlling proliferation and/or differentiation of a cell" encompasses the step of increasing the extent of growth and/or reproduction of the cell or specialization of the cell relative to an unmodulated cell either in vitro or in vivo. An increase or decrease in cell proliferation in cell culture can be detected by counting the number of cells before and after exposure to a molecule of interest. The extent of proliferation can be quantified via microscopic examination of the degree of confluency. Cell proliferation can also be quantified using a thymidine incorporation assay.

An increase or decrease in cell differentiation may be detected by identifying differentiated cell types which have specialized into various somatic or progenitor cell types. Identification may be carried out using cell markers known by the skilled addressee to identify cell types.

"Activity" as used herein relates to a function of a HA or HAS in a HSC cell, and includes the ability of HAS to synthesize HA or of HA to bind to chaperone, or upstream or downstream effector molecules thereby activating or repressing upstream or downstream pathways which affect proliferation or differentiation.

The term "modulating expression and/or activity" as used herein includes modifying or altering the expression and/or activity of HA or HAS, compared to unmodified levels of HA or HAS. Expression and/or activity may be increased or decreased compared to unmodified levels to increase or decrease proliferation or differentiation.

Modulation of HA or HAS expression and/or activity in the HSC may be achieved using antagonists, inhibitors, mimetics or derivatives of the HA or HAS. The terms "antagonist" or "inhibitor", as used herein, refer to a molecule which, when bound to either HA or HAS, blocks or modulates the activity of HA or HAS. Antagonists and inhibitors may include proteins, nucleic acids, carbohydrates, antibodies or any other molecules including ligands which bind to HA or HAS. A suitable ligand is HABP which may bind to HA. Proteins may include enzymes such as hyaluronidase which can break down HA and therefore affect the level of HA exposed on the HSC. Other modulators of the activity and/or expression of HA or HAS include a range of rationally-designed, synthetic inhibitors.

A suitable concentration of HABP is in the range of 5-20 µg/ml. In the case of hyaluronidase this may be used at 0.1 units per ml for approximately 15 min at room temperature or equivalent condition.

Modulation may be an increase or a decrease in expression and/or activity of an HAS gene or HAS activity, a change in binding characteristics, or any other change in the biological, functional or immunological properties. Modulators include, but are not limited to upstream and downstream regulators of HAS for expression and activity of the enzyme.

The term "mimetic", as used herein, refers to a molecule, the structure of which is developed from knowledge of the structure of HA or HAS or portions thereof and, as such, is able to effect some or all of the actions of HA or HAS-like molecules.

Modulation of HA or HAS expression and/or activity may be achieved by direct or indirect methods. Modulation of expression and/or activity of HA or HAS may be achieved using direct methods known to those of skill in the art and include, but are not limited to, knockout technology, antisense technology, triple helix technology, targeted mutation, gene therapy, regulation by agents acting on transcription. Indirect methods for modulating expression and/or activity of HA or HAS may include targeting upstream or downstream regulators such as cytokines.

Inhibition of expression and/or activity of HA or HAS may be achieved using a wide variety of inhibitors that target HA or HAS expression and/or activity either directly or indirectly. Inhibition may be achieved by inhibiting upstream or downstream targets involved in HA or HAS function.

In another aspect of the present invention, there is provided a method of treating a HSC associated condition comprising administering an effective amount of a composition comprising an enriched population of HSC or progeny thereof and wherein said HSC or progeny thereof, said enriched population of HSC or progeny thereof prepared by the methods described herein.

A "HSC associated condition" as used herein means any condition which results from an interaction with HSC or progeny thereof or is dependent upon HSC or progeny thereof. Examples of the HSC associated conditions may include anemia (including macrocytic and aplastic anemia); thrombocytopenia; hypoplasia; disseminated intravascular coagulation (DIC); myelodysplasia; immune (autoimmune) thrombocytopenic purpura (ITP); and HIV induced ITP and malignant conditions including leukaemia.

"Treatment" refers to both therapeutic treatment and prophylactic or preventative measures. Those in need of treatment include those already with the disease or disorder as well as those in which the disease or disorder is to be prevented.

The compositions of the present invention which comprise HSC or progeny hereof isolated by the described methods can find use in a number of ways.

These cells can be used to fully reconstitute an immunocompromised host such as an irradiated host and/or a host subject to chemotherapy; or as a source of cells for specific lineages, by providing for their maturation, proliferation and differentiation into one or more selected lineages by employing a variety of factors, including, but not limited to, erythropoietin, colony stimulating factors, e.g., GM-CSF, G-CSF, or M-CSF, interleukins, e.g., IL-1, -2, -3, -4, -5, -6, -7, -8, etc., or the like, or stromal cells associated with the HSCs or progeny thereof becoming committed to a particular lineage, or with their proliferation, maturation and differentiation.

HA and HAS has been found to be involved in the spatial distribution of the cells following transplantation. Treatment of the cells with hyaluronidase affects the spatial distribution of the cells. Hence, cells used for transplantation or reconstitution of patient's hematopoietic system may be pretreated with compounds which inhibit the removal of HA or preserve the level of expression of HA or HAS to achieve a normal cell type and distribution.

The HSCs and progeny thereof can also be used in the isolation and evaluation of factors associated with the differentiation and maturation of hematopoietic cells. Thus, the invention encompasses the use of hematopoietic stem cells in assays to determine the activity of media, such as conditioned media, or to evaluate fluids for cell growth activity, involvement with dedication of particular lineages, or the like.

The HSCs can be used for the treatment of genetic diseases. Thus, the invention encompasses treatment of genetic diseases associated with HSCs by genetic modification of autologous or allogeneic stem cells to correct the genetic defect. For example, diseases including, but not limited to, beta.-thalassemia, sickle cell anemia, adenosine deaminase deficiency, recombinase deficiency, recombinase regulatory gene deficiency, etc. may be corrected by introduction of a wild-type gene into the haematopoietic stem cells, either by homologous or random recombination.

In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo.

Other indications of gene therapy include introduction of drug resistance genes to enable normal stem cells to have an advantage and be subject to selective pressure during chemotherapy. Suitable drug resistance genes include, but are not limited to, the gene encoding the multi-drug resistance (MDR) protein.

Diseases other than those associated with hematopoietic cells can also be treated by genetic modification, where the disease is related to the lack of a particular secreted product including, but not limited to, hormones, enzymes, interferons, growth factors, or the like. By employing an appropriate regulatory initiation region, inducible production of the deficient protein can be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

In yet another aspect of the present invention there is provided a method of treating a HSC associated condition wherein said condition results from uncontrolled proliferation of HSCs or progeny thereof, said method comprising controlling expression of HA or HAS or a fragment thereof in a HSC or progeny thereof.

In a preferred aspect of the present invention there is provided a method of treating a HSC associated condition wherein said condition results from uncontrolled proliferation of HSCs or progeny thereof, said method comprising reducing expression and/or activity of HA or HAS or a fragment thereof in a HSC or progeny thereof.

Typical conditions in which uncontrolled proliferation occurs is in malignant conditions such as leukaemia including acute myeloid leukaemia (AML) and chronic myeloid leukaemia (CML).

The applicants have shown human leukemic cells exhibit elevated levels of HA. Specifically, human leukemic cell lines (HL-60, Mo7e and K562) express one or more HAS genes and synthesise high levels of HA which is efficiently removed by hyaluronidase. In addition, increased HA synthesis by leukemic blasts from patient AML, CML, acute lymphoid leukaemia (ALL), chronic lymphoid leukaemia (CLL), PLL, chronic monmoylocytic leukaemia (CMML), bi-phenotypic, and Hairy Cell leukemic samples (Table 1 has been shown).

Expression of HA on Leukaemic samples

| Disease | Number of patients analysed | % samples with elevated HA | % of leukaemic cells expressing HA |
|---|---|---|---|
| CLL | 8 | 8/8 | 2****/1**/3* |
| AML | 10 | 10/10 | 5****/2***/2* |
| ALL | 2 | 2/2 | 2* |
| CML | 8 | 7/8 | 1****/1* |
| CMML | 4 | 4/4 | 1****/1***/1**/1* |
| PLL | 2 | 2/2 | 1****/1** |
| Bi-phenotypic | 1 | 1/1 | 1**** |
| Hairy Cell | 2 | 1/2 | 1**** |

Figure 6:
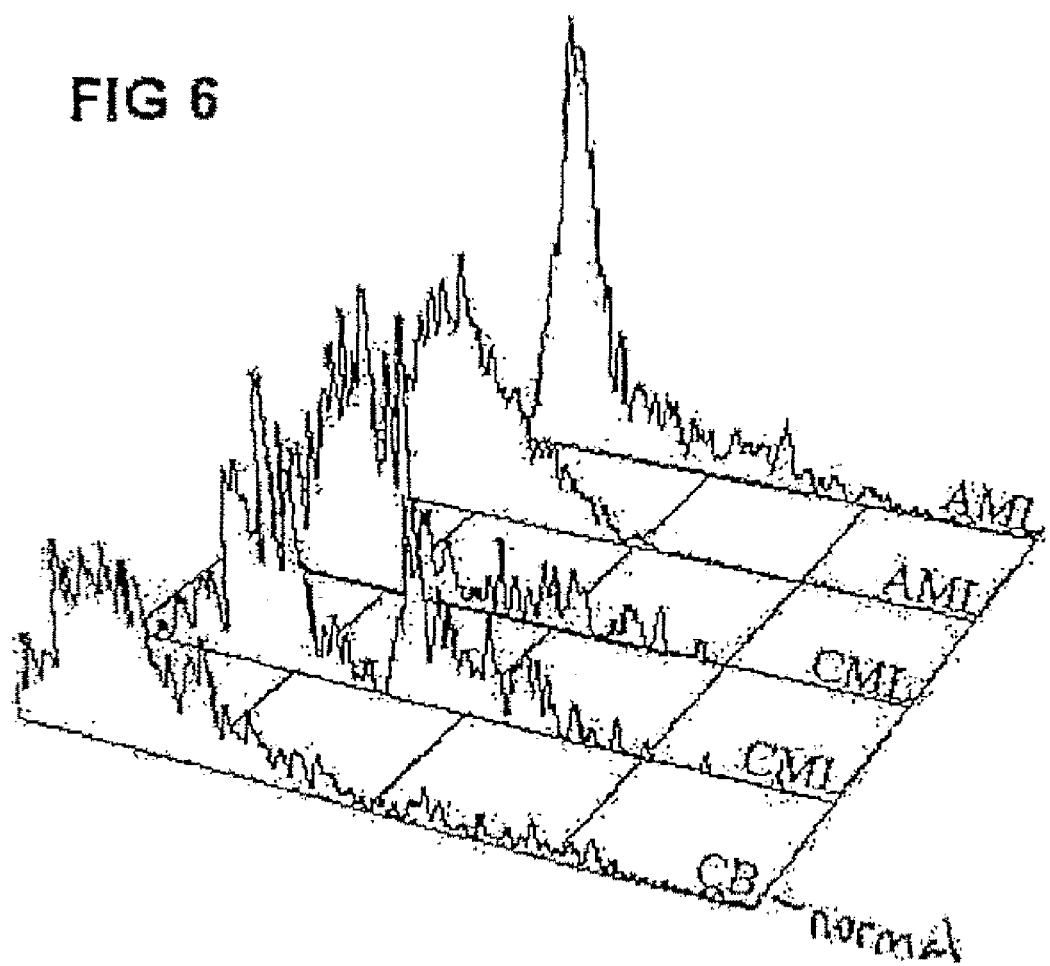
FIG. 6 shows maintenance of CD34$^+$ expression of cells cultured in the presence of various concentrations of HABP.

****75-100% leukaemic cells
***50-75% leukaemic cells
**25-50% leukaemic cells
*<25% leukaemic cells Compared to normal cord blood CD34$^+$ cells, the majority of leukemic cells exhibited an up regulation of the number of blast cells expressing HA. A distinct population of CML CD34$^+$ cells also expressed significantly higher levels of cell surface HA (FIG. 6). Patient samples all express HAS1, but limited samples express HAS2 and/or HAS3.

Accordingly in these leukaemias, HA and HAS are expressed at high levels. Controlling the level of HA expression can affect the proliferation of these cells. Decreasing the level of expression of HA can decrease the level of proliferation. This may be achieved by any of the methods described above for modulating the expression and/or activity of HA or HAS.

To treat the patient, a suitable modulator may be administered. The modulator may be administered by a variety of routes, including but not limited to, nasally, orally, transdermally, intramuscularly, intraperitoneally, subcutaneously, or intravenously.

This may be facilitated by using function-blocking antibodies, or agents that bind to HAS and therefore prevent HA synthesis. Alternatively cells may be retrovirally transduced cells with HAS antisense.

In yet another aspect of the present invention there is provided a method of treating a HSC associated condition wherein said condition results from differentiation of HSCs or progeny thereof, said method comprising controlling expression and/or activity of HA or HAS or a fragment thereof in a HSC or progeny thereof.

Like proliferation, differentiation is affected by expression of HA or HAS in HSC or progeny thereof.

In a preferred aspect of the present invention there is provided a method of treating a HSC associated condition wherein said condition results from differentiation of HSCs or progeny thereof, said method comprising reducing expression and/or activity of HA or HAS or a fragment thereof in a HSC or progeny thereof.

By reduction of differentiation using suitable modulators of HA or HAS expression and/or activity, differentiation can be controlled particularly in cancers which result from uncontrolled differentiation. Modulation may be conducted as described above.

Examples of the procedures used in the present invention will now be more fully described. It should be understood, however, that the following description is illustrative only and should not be taken in any way as a restriction on the generality of the invention described above.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Experimental (a) Umbilical Cord Blood. Cord blood (CB) samples were obtained following informed consent after normal and caesarian section deliveries at the Mercy Hospital for Women (East Melbourne, Australia).

(b) Mice. Six to 8 week old BALB/c H-2D, and congenic C57Bl/6J (Ly5.2) and PTRPA (Ly5.1) mice were purchased from Animal Resources Center (Perth, WA, Australia) and housed clean conventionally for at least a week prior to experimental use. CD44$^{-/-}$ mice (2) were kindly donated by Dr Tak Mak (Amgen Institute, Ontario Cancer Institute, University of Toronto). All mice received mouse chow (Barastok, St. Arnaud, Victoria, Australia) and acidified water ad libitum.

(c) Irradiation. The ability of cells to reconstitute hemopoiesis was analyzed in mice receiving a near-lethal dose of irradiation (9.5 Gy) in two equal fractions separated by a 4 hr interval, delivered from 2 opposing $^{137}$Cs sources (Gammacell 40; Atomic Energy of Canada, Ottawa, Canada) at a dose-rate of 1.4 Gy/min.

(d) Isolation of hemopoietic cells. Mice were killed by cervical dislocation. BM was routinely collected from femurs, tibiae and iliac crests. These bones were thoroughly ground in phosphate buffered saline (PBS) supplemented with 2% heat inactivated (HI) fetal calf serum (FCS; Hyclone, Logan, Utah). The bone fragments were washed multiple times, and the supernatant cell suspension and wash fractions were filtered through a 40 µm filter (Becton Dickinson, Franklin Lakes, N.J.) to remove large bone particles. The marrow was centrifuged (400 g, 5 min) and resuspended in fresh buffer. The cell supernatant was refiltered through a 40 µm filter, and diluted to $10^7$ cells/ml PBS supplemented with 2% HI FCS (buffer).

(e) Hemopoietic cell enrichment strategies.

(i) Murine. Bone marrow mononuclear cells of low density ($<1.0777$ g/cm$^3$) were isolated by discontinuous density centrifugation using Nycoprep for animals (Accurate Chemical and Scientific Corporation, Westbury, N.Y.). The isolated cells were washed in buffer prior to further manipulation. Lin$^-$ cells were isolated in a similar manner to that previously described (1). Briefly, low density cells were labelled with a cocktail of biotinylated or unconjugated primary rat anti-mouse antibodies: anti-B220 (CD45R; B cells); anti-Mac-1 (CD11b; macrophages); anti-Gr-1 (Ly-6G; neutrophils); anti-Lyt-2 (CD8), anti-L3T4 (CD4), anti CD3, and anti CD5 (T cells); and anti-Ter119 (erythroid cells). Each batch of antibody was evaluated by flow cytometric analysis for the concentration that resulted in the greatest shift in mean channel fluorescence and/or the percentage positive cells detected. Fifty microliters of double strength antibody cocktail was added per $5 \times 10^6$ cells suspended in an equal volume of buffer and the cell:antibody suspension incubated on ice for 20 minutes. Lin$^+$ cells were removed by immunomagnetic selection using the MACS system (Miltenyi Biotec, Bergisch, Gladbach, Germany) as previously described (1). In brief, washed, antibody labeled cells were incubated with goat anti-rat IgG microbeads (Miltenyi Biotec) at 4° C. for 15 minutes by adding 13 µl of beads to 87 µl of cell suspension (containing $10^7$ cells in buffer). The cells were washed in buffer, and resuspended in 1.5 ml of PBS, 5 mM EDTA, and 1% bovine serum albumin (BSA)/$10^8$ cells. Up to 2 ml of the cells were then added to the column (D column, maximum capacity $1 \times 10^9$ cells, generally not run at more than half the maximum stated capacity), run into the mesh, and left to magnetize for 5 minutes. The Lin$^-$ cells (non-magnetic fraction) were collected by eluting the cells through a 20-gauge needle with 50 mls of PBS, 5 mM EDTA, and 1% BSA.

(ii) Rhodamine123 (Rh) labelling. Lin$^-$ cells were washed in buffer, resuspended at $1 \times 10^6$/ml and incubated in a final Rh (Molecular Probes, Eugene, Oreg.) concentration of 0.1 µg/ml (diluted in buffer) for 20 minutes at 37° C. in the dark. The cells were centrifuged, resuspended at $10^6$ cells/ml, allowed to efflux for 15 min at 37° C. in the dark, centrifuged, and resuspended at $10^8$ cells/ml in PBS 0.5% HI FCS. Cells were incubated with a final concentration of 1:80 (6.8 µg/ml) goat anti-rat phycoerythrin (PE) conjugated secondary antibody (Biosource International; Camarillo, Calif.) on ice, in the dark for a further 20 minutes. Finally, the cells were washed in buffer, resuspended at $5 \times 10^6$ cells/ml and stored on ice prior to fluorescence activated cell sorting (FACS).

(iii) Stem Cell Antigen 1 (Sca-1) and c-kit labeling. Lin$^-$ cells were washed, centrifuged, and resuspended in a cocktail of Sca-1 FITC (Pharmingen; 1 µg/$5 \times 10^6$ cells) and c-kit PE (Pharmingen; 1 µg/$5 \times 10^6$ cells), and strepavidin-Red 670 (Gibco; 1/160 final concentration) on ice in the dark for 20 min. Finally, the cells were washed in buffer, resuspended at $5 \times 10^6$ cells/ml and stored on ice prior to fluorescence activated cell sorting (FACS).

(iv) Human. Mononuclear cells of low density were isolated from CB by discontinuous density centrifugation using Ficoll-Hypaque density gradient (d=1.077 g/ml, Pharmacia Biotech, Sweden) and washed 3 times by centrifugation at 400 g. The isolated cells were washed in PBS prior to further manipulation. Lin$^-$ cells were isolated as previously described. Briefly, cells were labeled with a cocktail of lineage antibodies including anti CD19, CD20, and CD24 (B cells and erythroid cells); anti CD3, CD2 and CD56 (T cells and NK cells); anti CD16, CD66b and CD11b (granulocytes and monocytes); anti CD14, CD36 (monocytes, platelets and erythroid cells). Lin$^+$ cells were removed by immunomagnetic selection using goat anti-mouse IgG microbeads and the MACS system as described above.

(v) CD34, CD38 and CD15 labelling. Lin$^-$ cells were washed, centrifuged, and resuspended in a cocktail of CD34 FITC and CD38PE, or CD15 FITC (Becton Dickinson, San Jose, Calif.; at the concentration recommended by the manufacturer) on ice in the dark for 20 min. Finally, the cells were washed in buffer, resuspended at $5 \times 10^6$ cells/ml and stored on ice prior to fluorescence activated cell sorting (FACS).

(f) Hyaluronic acid labeling. The presence of hyaluronic acid (HA) on the cell surface was detected using a final concentration of 20 µg/ml of biotinylated hyaluronic acid binding protein (HABP; Seikagaku, Tokyo, Japan) on ice for 20 min. Cells were washed, and labeled with strepavidin-PE or Red-670 (Gibco BRL, Grand Island, N.Y.) as described above.

(g) Hyaluronidase Treatment. To ensure that HABP labeling was specific, as well as to assess the importance of cell surface HA on the spatial distribution of engrafting cells, marrow sub-populations were treated with 0.1 U hyaluronidase (HY) (Sigma Aldrich) for 15 min at 21° C. to remove HA. Cells were washed in PBS 0.5% HI FCS.

(h) Flow cytometry. Labeled cells were sorted on a FACStar$^{plus}$ cell sorter equipped with a 5-watt argon ion laser (Coherent Innova 90, Palo Alto, Calif.) emitting 488 nm light at 200 mW, and a Spectra-Physics ultraviolet (UV) laser (Mountain View, Calif.) emitting 350/360 nm light at 50 mW. Light-scatter signals were collected through a 488-nm band pass 10 filter and a 1-decade logarithmic neutral density filter in the forward light scatter path. Rh emitted green fluorescence pulses were collected through an FITC 530-nm band pass 15 filter. Orange fluorescence pulses emitted following excitation of phycoerythrin (PE) were reflected through a 440 dichroic short pass mirror, and collected through a 575-nm band pass dichroic 26 filter. Pulses emitted following the excitation of Red 670 were collected through a long pass RG655 filter.

Cell Culture. Cells to be cultured were sorted directly into 96 well plates containing 100 µl of serum deprived media containing multiple cytokines and various concentrations of HABP. Murine cells were cultured in Iscove's Modified Dulbecco's Medium (Gibco BRL) containing 1% BSA, 10 µg/ml human insulin, 200 µg/ml human transferin, 0.05 mM 2-Mercaptoethanol and 21 µg/ml LDL. Human cells were cultured in X Vivo 10 media (Bio Whittaker, Verviers, Belgium) containing 0.5% buminate (Baxter, Glendale, Calif.).

(j) 5- (and-6)-carboxyfluorescein diacetate succinimidyl ester (CFSE) Labeling. Cells to be transplanted for spatial distribution analysis were labeled with the fluorescent dye CFSE (Molecular Probes, Eugene, Oreg.) as previously described (1). Briefly, cells were washed in PBS 0.5% HI FCS, resuspended in PBS 0.5% HI FCS at a density of $10^6$ cells/ml, and pre-incubated at 37° C. for 2 min. CFSE diluted to 5 mM in DMSO, and then to 5 µM in PBS was added to give a final concentration of 0.5 µM, and the dye solution cell mixture incubated at 37° C. for a further 10 min. Staining was stopped by adding 10 times the dye solution cell volume of ice cold PBS containing 20% FCS. Finally, the cells were washed in PBS, and resuspended for injection in up to 0.3 ml PBS per recipient.

(k) Transplants. Cells were transplanted by injection into the lateral tail vein. The actual numbers of cells injected were 500 $Lin^-$ $Sca^+$ $HA^+$ cells, 500 Lin– $Sca^+$ $HA^-$ cells, 5000-6000 $Lin^-$ $HA^+$ cells, 5-6×$10^5$ $Lin^-$ $HA^-$ cells, 1.1×$10^5$ $Lin^-$ $Rh^{dull}$ and 5.5×$10^5$ $Lin^-Rh^{bright}$ untreated and hyaluronidase treated cells.

(l) Analysis of transplanted cell spatial distribution. 15 hrs post-transplant, the spatial distribution of CFSE positive cells was analyzed as previously described (1). Briefly, BM was fixed by perfusing 2% paraformaldehyde, 0.05% glutaraldehyde through the descending aorta at physiological pressure. Femurs were removed and decalcified in 10% EDTA. Bones were then dehydrated embedded in paraffin. Three-and-a-half-µm longitudinal sections of each femur were cut and mounted in antifade mounting medium (Vectashield, Vector Laboratories). All sections were analysed under a fluorescence microscope (Zeiss, Camperdown, NSW, Australia) using an FITC and Texas red dual filter set (green excitation at 578 nm, and red excitation at 610 nm). This filter set was specifically chosen because the short emission band-widths enabled CFSE positive BM cells to be easily distinguished from host marrow cells.

The spatial distribution of transplanted cells was determined by analysing the location of CFSE labeled cells (positive cells) from at least 6 longitudinal sections per transplant recipient. Central longitudinal sections were analyzed as opposed to transverse sections, as each individual section encompasses more of the entire femur. To ensure that individual cells were only analyzed once, every alternate 3.5 µm section was analyzed. The location of positive cells were designated as either endosteal (previously arbitrarily defined as within 12 cells of the endosteum (3)) or central (greater than 12 cells from either endosteum) (1).

(m) RNA extraction. RNA was extracted using an RNAzol B (Bresatec, SA, Australia) extraction method. Briefly, cells were centrifuged, and RNA prepared by lysing the cells with 0.2 ml/$10^6$ cells of RNAzol B. The homogenate was chloroform extracted and isopropanol precipitated. RNA was washed, dried and resuspended in sterile water.

(n) Reverse transcriptase-polymerase chain reaction (RT-PCR). Template cDNA was prepared using random hexamers (Pharmacia Biotech, Uppsala, Sweden) and Superscript II reverse transcriptase (Gibco-BRL, Gaithersburg, Md.). PCR was performed using the following oligonucleotide primers: murine Has-1 sense (5' CGTGGACTACGTGCAGGTCT-GTG 3') (Seq ID No: 1) and antisense (5' GAGCGCGAGG-TATACTTGGTAGC 3') (Seq ID No: 2), murine Has-2 sense (5' GACCACACAGACAGGCGGA 3') (Seq ID No: 3) and antisense (5' TCCCAGGGTAGGTCAGCCTT 3') (Seq ID No: 4), murine Has-3 sense 3' 5' (5' GAGCGTGTGC GAGCTGTGGT GTG 3') (Seq ID No: 5) and antisense (5' GAAGCATCTCAATGGTGCAGGCT 3') (Seq ID No: 6), human HAS-1 sense (5' GCTACCAAGTACACCTCCAG-GTC 3') (Seq ID No: 7) and antisense (5' CGCGTAGAACA-GACGCAGCACAG 3') (Seq ID No: 8), human HAS-2 sense (5' GCTCGCAACACGTAACGCAA 3') (Seq ID No: 9) and antisense (5' GGCACTTAGATCGAGCTGTG 3') (Seq ID No: 10), and human HAS-3 sense (5' AGCCTGCAG-GAGGGCATGGA 3') (Seq ID No: 11) and antisense (5' GGAGCGCGCGGTATACTTAGTTCGG 3') (Seq ID No: 12) synthesized by Geneworks (Adelaide, SA, Australia). All PCR were performed in a 25 µl volume under 30 µl of paraffin oil in a gene machine (Innovonics, Melbourne, Australia). Each PCR consisted of 1× Taq gold buffer, 200 µM dNTPS (Boehringer Mannheim, Branchburg, N.J.), 4 µg/ml of each primer, 1.5 mM $MgCl_2$, 10% DMSO, and 0.5 U Taq Gold (Boehringer Mannheim). PCRs were performed with a profile of 10 min of Taq gold activation at 94° C. for the first cycle and 30 sec denaturing for subsequent cycles, 30 sec of annealing at 60° C. for 10 cycles followed by 30 sec of annealing at 55° C. for a further 25 cycles, and 30 sec extension at 72° C. for the 35 cycles followed by a final 5 min extension at 72° C.

Statistical analysis. Differences between means were evaluated by one-way analysis of variance (ANOVA) or students t-test where appropriate.

Example 1

HA Expression On Murine Hemopoietic Cells

Figure 2:
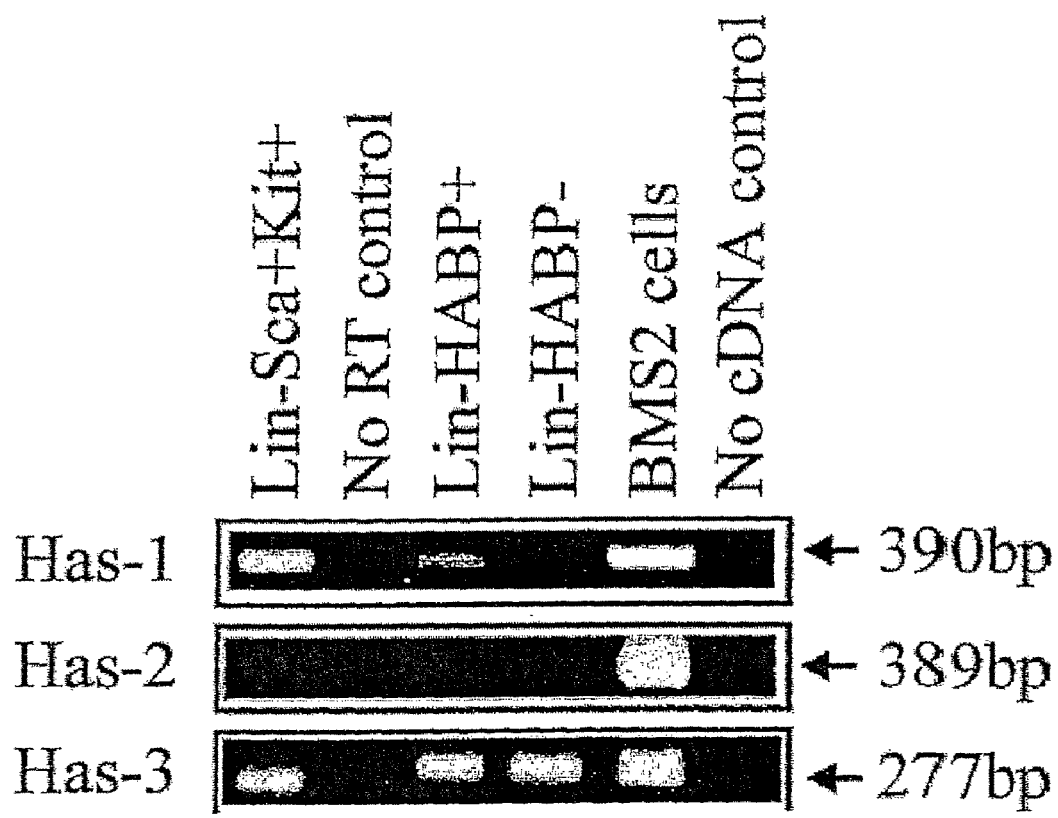
FIG. 2 shows expression of HAS genes in murine cells.

Expression of HA was demonstrated by flow cytometric analysis through the binding of a biotinylated form of hyaluronic acid binding protein (HABP), which demonstrates absolute specificity for HA (4). Using this approach, HABP binding was detected on two murine sub-populations enriched for HSC: $Lin^-Sca^+Kit^+$ (FIG. 1a) and $Lin^-Rh^{dull}$ and was completely eliminated by prior treatment of the cells with the enzyme hyaluronidase (HY) (FIG. 1b). In addition, a similar proportion of $Lin^-$ $Rh123^{dull}$ cells isolated from $CD44^{-/-}$ mice (2) exhibited binding of HABP (25.0% compared to 26.5%), demonstrating that HA detected on the cell surface is not due to the binding of exogenous HA to its major receptor CD44 (19) but due to de-novo synthesis by primitive hemopoietic cells themselves. Importantly, RT-PCR analysis demonstrated that $Lin^-Sca^+Kit^+$, $Lin^-HABP^+$ but not $HABP^-$ cells express Has-1, Has-2 and Has-3 (FIG. 2 a+b).

Example 2

HA Expression of Human HPC

Figure 3:
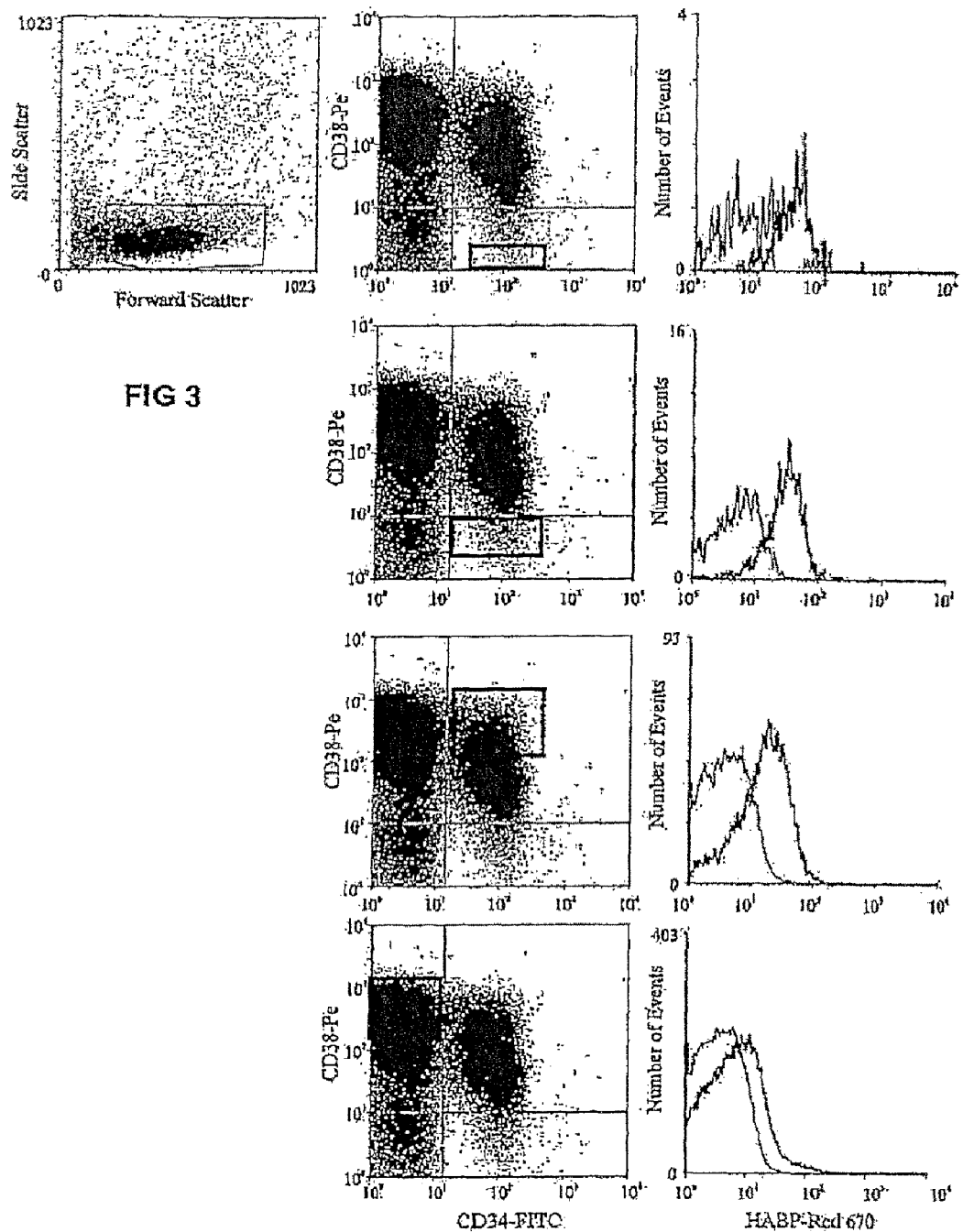
FIG. 3 shows HA expression on maturing CD34$^+$ cells.
Figure 4:
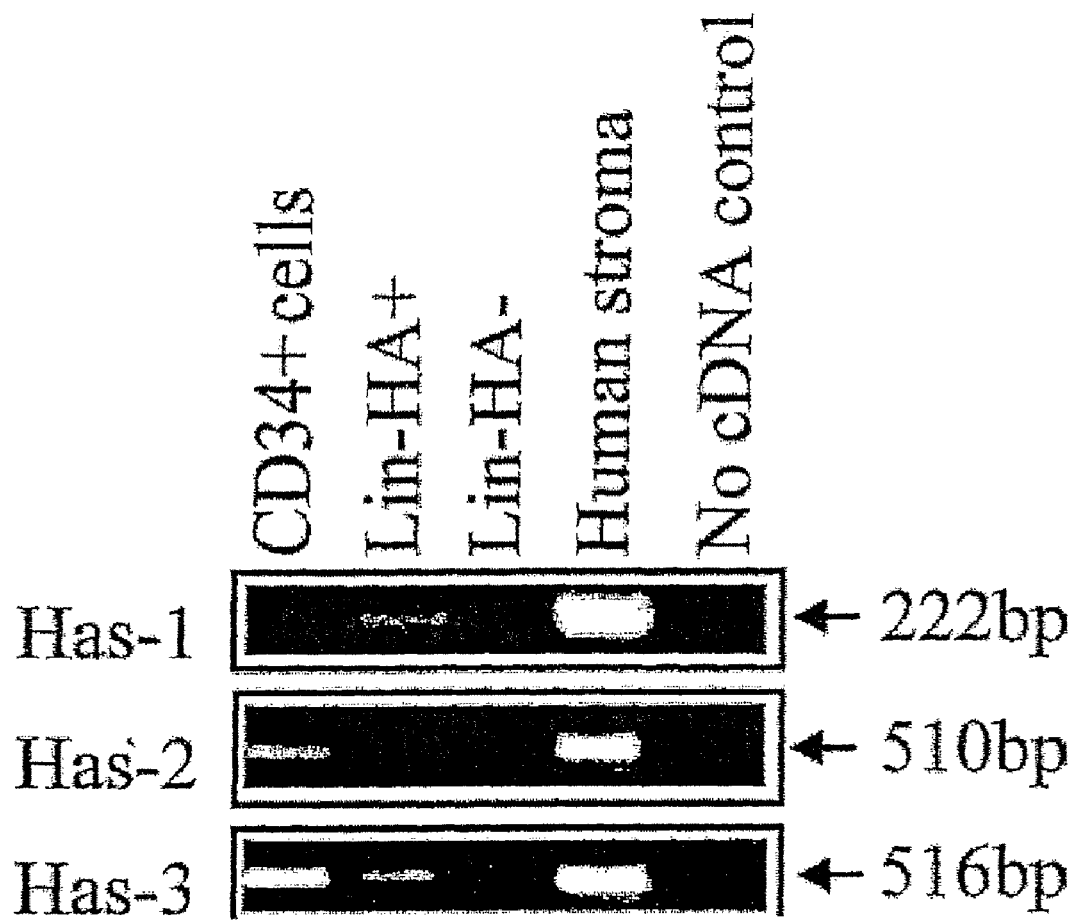
FIG. 4 shows HAS gene expression in human HSC.

The expression of HA by primitive BM cells is not a unique feature of the mouse but is also a characteristic of human hemopoietic progenitors. FACS analysis of human umbilical cord blood (CB) (FIG. 3) using CD34, CD38 and HABP showed putative Human HSC synthesise HA. Interestingly, there was a significant decrease in the level of HA expression in correlation with a maturing cell phenotype, with no HA expression detected on $CD34^-CD38^+$ cells. In accord with data in the mouse, isolated human $CD34^+$ and $Lin^-HA^+$ cells but not $Lin^-HA^-$ also express HAS1, HAS2 and HAS3 (FIG. 4). Collectively these data demonstrate that HA is synthesized by and expressed on murine and human hemopoietic populations enriched for HSC.

However, repopulating HSC represent only a minor proportion of $Lin^-Rh123^{dull}$ cells (5). In order to examine whether HSC were contained within the $HABP^+$ subpopulation, FACS was used to isolate $Lin^-HABP^+$ and $Lin^-HABP^-$, and Lin⁻Sca⁺HABP⁺ and Lin⁻Sca⁺HABP⁻ subpopulations and the cells assayed in vivo using the congenic Ly5.1/Ly5.2 mouse model (6). 5000-6000 Lin⁻HABP⁺ cells reconstituted all hemopoietic lineages in the peripheral blood (PB) of lethally irradiated recipients 8 weeks post-transplant (Table 2) while an equivalent number of Lin⁻HABP⁺ cells failed to do so, with the recipients dying 14-16 days post-transplant. In addition, transplantation of 500 Lin⁻Sca⁺HABP⁺ cells resulted in reconstitution of multiple hemopoietic lineages of lethally irradiated recipients 4 weeks post-transplant (Table 2). Thus HA is expressed on HSC with long-term repopulating potential, but the level of engraftment is significantly lower than predicted from infused un-fractionated Lin⁻Sca⁺ cells (7). However, in only one of six recipients were HABP⁻ cells capable of rescuing lethally irradiated recipients (following a transplant of 500 Lin⁻Sca⁺HABP⁻ cells), suggesting that the majority of HSC are not contained within this population. In the one surviving recipient, there was an equivalent proportion of donor cells to that seen following a transplant of the HA⁺ cells (~9%). The reason for this lower than expected level of engraftment remains unclear, but is suggestive of HA not simply playing a passive structural role, but also being a specific signal-inducing molecule.

TABLE 2

Analysis of the ability of Lin⁻ cells expressing HA to reconstitute hemopoiesis in vivo.

|   | % of each subpopulation within the donor cells detected following a transplant of Lin⁻HABP⁺ cells* | % of each subpopulation within the donor cells detected following a transplant of Lin⁻Sca⁺HABP⁺ cells* |
|---|---|---|
| MAC-1/GR-1 | 40 ± 3 | 68 |
| B220 | 36 ± 6 | UN |
| CD4/CD8 | 20 ± 3 | 22 |

Mice were injected with either 5000-6000 Lin⁻HABP⁺ cells (4 mice) or 500 Lin⁻Sca⁺HABP⁺ cells (2 mice) and analyzed 4-8 weeks post-transplant. Peripheral blood was collected, and the red blood cells lysed using ammonium chloride. The percentage donor cells was determined using LY5.1 antibody labeling, and was 9±1.7% and 9.4±0.02% following a transplant of 5000-6000 Lin⁻ HABP⁺ cells or 500 Lin⁻Sca⁺HABP⁺ cells respectively.

White blood cells were labeled for macrophages and granulocytes (MAC-1/GR-1), B cells (B220) and T cells (CD4/CD8) and the proportion of donor analyzed using an Ly5.1 antibody*.

UN unknown

Example 3

The Potential Role of HA as a Negative Regulator of HSC Proliferation

Figure 5A:
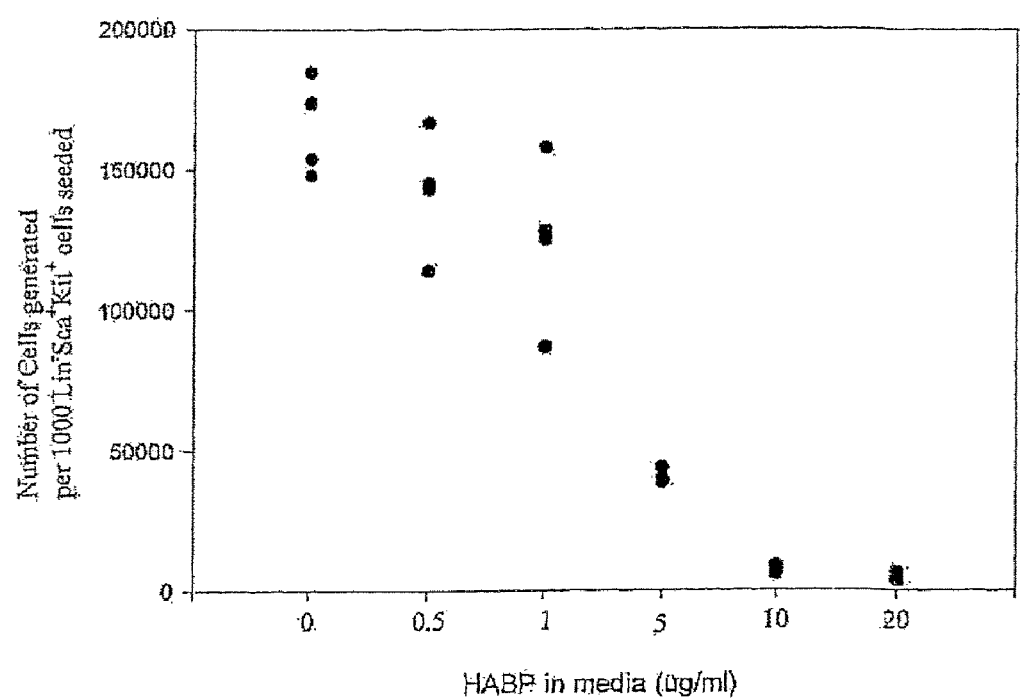
FIG. 5a(i) shows growth inhibition in murine HSC.
Figure 5B:
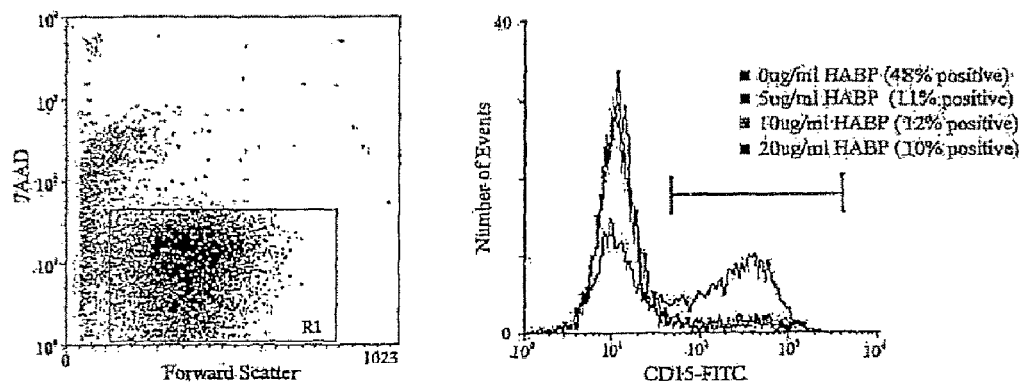
FIG. 5b(i) shows differentiation of cultured CD34$^+$ CD38$^-$ CB cell.

In vitro stroma-free, cytokine-dependent cultures demonstrated that the ligation of HA by a the surrogate soluble ligand HABP results in a profound suppression of both murine and human HSC proliferation while stimulated by a potent combination of early acting hemopoietic growth factors. Both murine and putative human HSC (Lin⁻Sca⁺Kit⁺ and Lin⁻CD34⁺CD38⁻ cells respectively) were cultured in serum free conditions in the presence of multiple cytokines consisting of either SCF (75 ng/ml), IL-11, FLT3 Ligand and IL-6 (all 100 ng/ml) or G-CSF, SCF, FLT3 Ligand, MGDF (all 100 ng/ml), II-6 and IL-3 (both 10 ng/ml) for murine and human HSC respectively, and various concentrations of HABP. As shown in FIG. 5 this resulted in a significant inhibition of cell proliferation corresponding to the presence of increasing concentrations of HABP. This unexpected data shows a marked growth inhibitory effect of HA on hemopoiesis. In addition to growth inhibition, as shown in FIG. 5a incubating HSC in increasing amounts of HABP maintained cells phenotypic of the input population and prevented cell differentiation. In contrast a significant proportion of cells cultured in the absence of HABP differentiated to become CD15 positive (FIG. 5b). This observed growth regulatory role is in accord with a recent report showing that the addition of HA in vitro results in perturbation of hemopoiesis (8). In this study, exogenous HA was added to LTBMC, resulting in enhanced production of both progenitors and mature BM cells, whereas the addition of HY resulted in the inhibition of cell production. In these cultures, HA was thought to be regulating hemopoiesis through a progenitor ancestral to the common myeloid and lymphoid progenitor. In addition this observed growth regulatory role of HA is very similar to that recently described for the sialomucin PSGL-1: P-Selectin interaction (9). In addition to its well-documented role as an adhesion molecule, PSGL-1 has now been shown to be a potent negative regulator of human hemopoietic progenitors.

Example 4

The Role of HA in the Spatial Distribution of Transplanted Murine HSC

Further recent data from our laboratory indicates that the expression of this CAM on HSC is functionally significant, being involved in regulating their lodgment post-transplant. When Lin⁻Rh$^{dull}$ cells were treated with HY prior to transplantation, there was an ~40% reduction in the number of cells located at the endosteum 15 hours post-transplant compared to untreated cells (39±3 and 65±8 respectively). In contrast, HY treatment of Lin⁻Rh$^{bright}$ cells, shown not to synthesize any of the Has genes (data not shown), did not alter their spatial distribution at the same time-point (41±3 and 37±4 respectively). This suggests a specific role in determining the spatial localization of HSC but not HPC.

Overall our data is the first demonstration of HSC synthesis and expression of HA in vitro and in vivo, representing a very specific but as yet unrecognized characteristic of primitive hemopoietic cells in at least two mammalian species. The presence of HA on HSC is functionally significant in stem cell biology, specifically in the regulation of HSC lodgment post-transplant. In addition, the data also suggests that the binding of HA on the surface of HSC to a surrogate ligand plays an important role in regulating the proliferation and differentiation of these cells.

REFERENCES

1. Nilsson, S. K., Johnston, H. M., Coverdale, J. A. 2001. Spatial localization of transplanted hemopoietic stem cells: inferences for the localization of stem cell niches. *Blood* 97: 2293.
2. Schmits, R., J. Filmus, N. Gerwin, G. Senaldi, F. Kiefer, T. Kundig, A. Wakeham, A. Shahinian, C. Catzavelos, J. Rak, C. Furlonger, A. Zakarian, J. J. Simard, P. S. Ohashi, C. J. Paige, J. C. Gutierrez-Ramos, and T. W. Mak. 1997. CD44 regulates hematopoietic progenitor distribution, granuloma formation, and tumorigenicity. *Blood* 90, no. 6: 2217.
3. Nilsson, S. K., M. S. Dooner, C. Y. Tiarks, H.-U. G. Weier, and P. J. Quesenberry. 1997. Potential and distribution of transplanted hematopoietic stem cells in a nonablated mouse model. *Blood* 89, no. 11: 4013.
4. Engstrom-Laurent, A., and R. Hallgren. 1985. Circulating hyaluronate in rheumatoid arthritis: relationship to inflammatory activity and the effect of corticosteroid therapy. *Ann Rheum Dis* 44, no. 2: 83.
5. Spangrude, G. J., S. Heimfeld, and I. L. Weissman. 1988. Purification and characterization of mouse hematopoietic stem cells. *Science* 241: 58.
6. Spangrude, G. J., and D. M. Brooks. 1993. Mouse strain variability in the expression of the hematopoietic stem cell antigen Ly-6A/E by bone marrow cells. *Blood* 82, no. 11: 3327.
7. Spangrude, G. J., and R. Scollay. 1990. A simplified method for enrichment of mouse hematopoietic stem cells. *Exp Hematol* 18, no. 8: 920.
8. Khaldoyanidi, S., A. Denzel, and M. Zoller. 1996. Requirement for CD44 in proliferation and homing of hematopoietic precursor cells. *Journal of Leukocyte Biology* 60: 579.
9. Levesque, J. P., A. C. Zannettino, M. Pudney, S. Niutta, D. N. Haylock, K. R. Snapp, G. S. Kansas, M. C. Berndt, and P. J. Simmons. 1999. PSGL-1-mediated adhesion of human hematopoietic progenitors to P-selectin results in suppression of hematopoiesis. *Immunity* 11, no. 3: 369.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method of identifying a subpopulation of $Lin^-HA^+$ haematopoietic stem cells (HSC) or progeny, thereof comprising the steps of:
   obtaining a cell sample including $Lin^-HA^+$ HSC or progeny thereof;
   detecting the presence of hyaluronic acid (HA) on a cell of the sample by exposing or combining the cell sample with a marker for HA wherein the marker identifies HA on the cell surface; and
   identifying as a HSC or progeny thereof a cell having HA on the cell.

2. The method according to claim 1 wherein the marker further comprises a label which enhances identification of the marker.

3. The method according to claim 2 wherein the marker is selected from the group consisting of a fluorescent, radioactive and enzymatic label.

4. A method according to claim 1 wherein the sample is enriched for $CD34^+$ cells prior to the detecting.

5. The method according to claim 2 wherein the marker is a fluorescent label.

* * * * *

UNITED STATES PATENT AND TRADEMARK OFFICE
CERTIFICATE OF CORRECTION

PATENT NO. : 7,718,379 B2
APPLICATION NO. : 11/933633
DATED : May 18, 2010
INVENTOR(S) : Susan Kaye Nilsson Page 1 of 1

It is certified that error appears in the above-identified patent and that said Letters Patent is hereby corrected as shown below:

Please correct the related U.S. Application Data to read as follows:

(63) Continuation of application number 10/837,038, filed Aug. 30, 2004 (now abandoned), which is a continuation-in-part of application No. PCT/AU02/01443 filed on October 24, 2002.

Signed and Sealed this
Eighteenth Day of January, 2011

David J. Kappos
*Director of the United States Patent and Trademark Office*

SEQUENCE LISTING

```
<160> NUMBER OF SEQ ID NOS: 12

<210> SEQ ID NO 1
<211> LENGTH: 23
<212> TYPE: DNA
<213> ORGANISM: Musa sp.

<400> SEQUENCE: 1
cgtggactac gtgcaggtct gtg                                           23

<210> SEQ ID NO 2
<211> LENGTH: 23
<212> TYPE: DNA
<213> ORGANISM: Musa sp.

<400> SEQUENCE: 2
gagcgcgagg tatacttggt agc                                           23

<210> SEQ ID NO 3
<211> LENGTH: 19
<212> TYPE: DNA
<213> ORGANISM: Musa sp.

<400> SEQUENCE: 3
gaccacacag acaggcgga                                                19

<210> SEQ ID NO 4
<211> LENGTH: 20
<212> TYPE: DNA
<213> ORGANISM: Musa sp.

<400> SEQUENCE: 4
tcccagggta ggtcagcctt                                               20

<210> SEQ ID NO 5
<211> LENGTH: 23
<212> TYPE: DNA
```

<213> ORGANISM: Musa sp.

<400> SEQUENCE: 5 gagcgtgt gcgagctgtg gtgtg    23

<210> SEQ ID NO 6
<211> LENGTH: 23
<212> TYPE: DNA
<213> ORGANISM: Musa sp.

<400> SEQUENCE: 6
gaagcatctc aatggtgcag gct    23

<210> SEQ ID NO 7
<211> LENGTH: 23
<212> TYPE: DNA
<213> ORGANISM: Musa sp.

<400> SEQUENCE: 7
gctaccaagt acacctccag gtc    23

<210> SEQ ID NO 8
<211> LENGTH: 23
<212> TYPE: DNA
<213> ORGANISM: Musa sp.

<400> SEQUENCE: 8
cgcgtagaac agacgcagc acag    23

<210> SEQ ID NO 9
<211> LENGTH: 20
<212> TYPE: DNA
<213> ORGANISM: Musa sp.

<400> SEQUENCE: 9
gctcgcaaca cgtaacgcaa    20

<210> SEQ ID NO 10
<211> LENGTH: 20
<212> TYPE: DNA
<213> ORGANISM: Musa sp.

<400> SEQUENCE: 10
ggcacttaga tcgagctgtg    20

<210> SEQ ID NO 11
<211> LENGTH: 20
<212> TYPE: DNA
<213> ORGANISM: Musa sp.

<400> SEQUENCE: 11
agcctgcagg agggcatgga    20

<210> SEQ ID NO 12
<211> LENGTH: 25
<212> TYPE: DNA
<213> ORGANISM: Musa sp.

<400> SEQUENCE: 12 ggagcgcg cggtatactt agttcgg    25